(12) United States Patent
Bernabeu Martínez et al.

(10) Patent No.: US 9,181,260 B2
(45) Date of Patent: Nov. 10, 2015

(54) CRYSTALLINE FORM OF SITAGLIPTIN SULFATE

(71) Applicant: MOEHS IBERICA S.L., Rubí-Barcelona (ES)

(72) Inventors: Maria del Carmen Bernabeu Martínez, Rubí-Barcelona (ES); Alicia Dobarro Rodríguez, Rubí-Barcelona (ES); Cristobal Galán Rodríguez, Rubí-Barcelona (ES)

(73) Assignee: MOEHS IBERICA, S.L., Rubi-Barcelona (ES)

( * ) Notice: Subject to any disclaimer, the term of this patent is extended or adjusted under 35 U.S.C. 154(b) by 0 days.

(21) Appl. No.: 14/381,954

(22) PCT Filed: Mar. 1, 2013

(86) PCT No.: PCT/EP2013/054164
§ 371 (c)(1),
(2) Date: Aug. 28, 2014

(87) PCT Pub. No.: WO2013/128000
PCT Pub. Date: Sep. 6, 2013

(65) Prior Publication Data
US 2015/0037406 A1    Feb. 5, 2015

(30) Foreign Application Priority Data

Mar. 2, 2012   (ES) .................................. 201230319

(51) Int. Cl.
*A61K 9/20*   (2006.01)
*A61K 9/28*   (2006.01)
(Continued)

(52) U.S. Cl.
CPC ............ *C07D 487/04* (2013.01); *A61K 9/2013* (2013.01); *A61K 9/2018* (2013.01); *A61K 9/2027* (2013.01); *A61K 9/2054* (2013.01); *A61K 9/28* (2013.01); *A61K 31/155* (2013.01); *A61K 31/4985* (2013.01); *A61K 45/06* (2013.01); *A61K 31/22* (2013.01);
(Continued)

(58) Field of Classification Search
CPC . A61K 2300/00; A61K 31/155; A61K 31/22; A61K 31/404; A61K 31/4439; A61K 31/4985; A61K 31/64; A61K 45/06; A61K 9/2013; A61K 9/2018; A61K 9/2027; A61K 9/2054; A61K 9/28; C07D 487/04
See application file for complete search history.

(56) References Cited

FOREIGN PATENT DOCUMENTS

WO    03/004498 A1    1/2003
WO    2004/085378 A1    10/2004
(Continued)

OTHER PUBLICATIONS

Remington: The Science and Practice of Pharmacy, 22nd Edition, 2012, The Science of Pharmacy pp. 1049-1070.
(Continued)

*Primary Examiner* — Aradhana Sasan
(74) *Attorney, Agent, or Firm* — Tristan A. Fuierer; Moore & Van Allen, PLLC

(57) ABSTRACT

A novel crystalline form of sitagliptin sulfate is provided. In addition, a method for obtaining the crystalline form, pharmaceutical compositions comprising the novel crystalline form and the crystalline form for use as a medicament are provided.

20 Claims, 19 Drawing Sheets

(51) Int. Cl.
*A61K 31/155* (2006.01)
*A61K 31/22* (2006.01)
*A61K 31/404* (2006.01)
*A61K 31/4439* (2006.01)
*A61K 31/4985* (2006.01)
*A61K 31/64* (2006.01)
*A61K 45/06* (2006.01)
*C07D 487/04* (2006.01)

(52) U.S. Cl.
CPC .......... *A61K 31/404* (2013.01); *A61K 31/4439* (2013.01); *A61K 31/64* (2013.01)

(56) References Cited

FOREIGN PATENT DOCUMENTS

| WO | 2005003135 A1 | 1/2005 |
|----|---------------|--------|
| WO | 2005/067976 A2 | 7/2005 |
| WO | 2005/072530 A1 | 8/2005 |
| WO | 2007/035198 A2 | 3/2007 |
| WO | 2009/064476 A1 | 5/2009 |
| WO | 2009/085990 A2 | 7/2009 |
| WO | 2010/000469 A2 | 1/2010 |
| WO | 2010/092090 A2 | 8/2010 |
| WO | 2010117738 A2 | 10/2010 |
| WO | 2011/123641 A1 | 10/2011 |

OTHER PUBLICATIONS

Remington: The Science and Practice of Pharmacy, 2nd Edition, 2012, vol. 1: The Science of Pharmacy pp. 947-976.
International Search Report dated Jun. 25, 2013 for PCT/EP2013/054164.
Kim, Dooseop et al. "(2R)-4-Oxo-4[3-(Trifluoromethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes", J. Med. Chem. 2005 48(1) 141-151.
Mino R. Caira, "Crystalline Polymorphism of Organic Compunds," Topics in Current Chemistry, 1998, pp. 163-208.

CRYSTALLINE FORM OF SITAGLIPTIN SULFATE

CROSS REFERENCE TO RELATED APPLICATIONS

This application is the U.S. National Phase of International Application No. PCT/EP2013/054164, filed Mar. 1, 2013, designating the U.S. and published in English as WO 2013/128000 on Sep. 6, 2013 which claims the benefit of Spain Patent Application No. 201230319, filed Mar. 2, 2012.

FIELD OF THE INVENTION

The present invention relates to a novel crystalline form of the addition salt of sitagliptin with sulfuric acid, to processes for obtaining the same, to pharmaceutical compositions comprising said crystalline form and to methods for treating type 2 diabetes which comprise administering said pharmaceutical compositions to patients.

BACKGROUND OF THE INVENTION

Sitagliptin, the chemical name of which is (2R)-4-oxo-4-[3-(trifluoromethyl)-5,6-dihydro[1,2,4]triazol[4,3-α]pyrazin-7(8H)-yl]-1-(2,4,5-trifluorophenyl)butan-2-amine, is a member of a class of antihyperglycemic agents called dipeptidyl peptidase 4 (DPP-IV) inhibitors which improve blood glucose control in type 2 diabetes patients by increasing the concentrations of incretin hormones. These hormones, including glucagon-like peptide-1 (GLP-1) and glucose-dependent insulinotropic peptide (GIP), are released by the intestine throughout the day and their concentrations increase in response to food intake. The activity of GLP-1 and of GIP is limited by the DPP-IV enzyme which quickly hydrolyzes incretins and transforms them into inactive products. Sitagliptin prevents this incretin hydrolysis by DPP-IV, so plasma concentrations of active forms of GLP-1 and GIP increase. As a result, sitagliptin increases insulin release and reduces the concentration of glucagon in a glucose dependent manner.

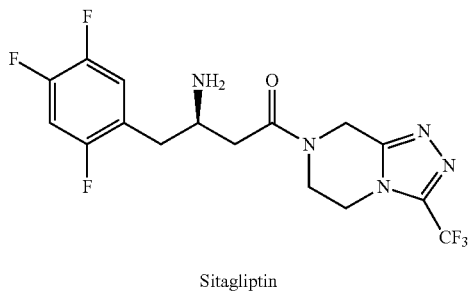 [SMILES: N[C@@H](CC(=O)N1CCn2c(nnc2C(F)(F)F)C1)Cc1cc(F)c(F)cc1F]

Sitagliptin

Sitagliptin was commercially authorized by the European Medicines Agency in March 2007. The medicinal product is currently marketed under the name Januvia®, being formulated with the dihydrogen phosphate salt of sitagliptin.

European patent EP 1412357 B1 (WO 2003/004498 A2) protects sitagliptin and its pharmaceutically acceptable salts. Likewise, in relation to the marketed medicinal product, a subsequent European patent EP 1654263 B1 (WO 2005/003135 A2) (MERCK; Jul. 18, 2004) specifically protects the dihydrogen phosphate salt of sitagliptin.

It is known by the person skilled in the art that different salts of one and the same pharmaceutically active substance can have different physical properties (melting point, solubility, hygroscopicity, etc). Even the existence of different crystalline forms of one and the same salt of one and the same pharmaceutically active substance can also have considerably different physical properties. Said differences can accordingly influence the pharmaceutical properties of the medicinal product formulated with the crystalline forms, without the person skilled in the art being able to predict a priori the existence of these crystalline forms or the different physical characteristics that they may have.

In this respect, several documents of the state of the art have described the existence of different crystalline forms of the addition salt of sitagliptin with sulfuric acid.

International application WO 2009/085990 A2 describes the production of an anhydrous crystalline form of sitagliptin sulfate salt and its characterization by means of DSC (Differential Scanning calorimetry), TGA (Thermal Gravimetric Analysis) and XRPD (X-Ray Powder Diffraction). However and in the hands of the inventors of the present application, said crystalline form is hygroscopic under the conditions of the European Pharmacopeia Ed. 6.0 Section 5.11 (24 hours at 80% RH and 25° C.), readily reaching a water proportion corresponding to a dihydrate form.

International application WO 2010/000469 A2 describes the production of an ethanol solvate (Form I) and of a crystalline form of sitagliptin sulfate salt (Form II). Both forms were characterized by means of DSC and XRPD, Form II having a water content corresponding to a monohydrate compound. This same form quickly reaches greater degrees of hydration (Table 21 of the application) under 43% and 75% relative humidity conditions, indicating the hygroscopic characteristics thereof.

International application WO 2010/092090 A2 describes the production of a crystalline form of sitagliptin sulfate salt, the characterization of which by means of XRPD is consistent with the crystalline form described in International application WO 2009/085990 A2.

Finally, international applications WO 2010/117738 A1 and WO 2011/123641 A1 describe the production of 19 crystalline forms (called S1 to S20 except form S15 which is not described) of sitagliptin sulfate salt (some of them, for example S4 and S5, being those previously described in the applications indicated above). The crystalline forms of these two applications are mainly characterized by means of their corresponding XRPD. According to the inventors, forms S7 and S13 are isopropanol solvate and methanol solvate, respectively. Crystalline form S14 is a monohydrate, crystalline form S16 is a sesquihydrate and crystalline forms S1, S9 and S11 are dihydrates. Despite not further describing physical properties of the remaining crystalline forms, there is data relating to same which indicate that crystalline forms S2 and S6 are transformed into form S9 under 100% relative humidity conditions, crystalline forms S13 and S16 and S18 are transformed into crystalline forms S14, S17 and S14, respectively, when the wet compound residual solvent is dried in a standard manner, crystalline form S17 is transformed into form S14 by being kept at a temperature of 50° C. (24 hours) or form S14 is transformed into form S1 or into a mixture of forms S1 and S11 when they are subjected to an environment with a high relative humidity. They also describe that under standard wet compound residual solvent drying conditions, crystalline form S11 is transformed into form S12, crystalline form S16 is transformed into crystalline form S17, which in turn is transformed into crystalline form S14, crystalline form S18 is transformed into crystalline form S14. Furthermore, patent application WO 2011/123641 A1 states that crystalline forms S7 and S10 filter slowly.

Based on what is described in the state of the art, it is necessary to obtain a crystalline form of the addition salt of sitagliptin with sulfuric acid with physical characteristics that allows it to be formulated in pharmaceutical compositions with assured stability.

SUMMARY

Therefore, an object of the present invention is to provide a novel crystalline form of the addition salt of sitagliptin with sulfuric acid (1:1), having improved physical and pharmaceutical properties

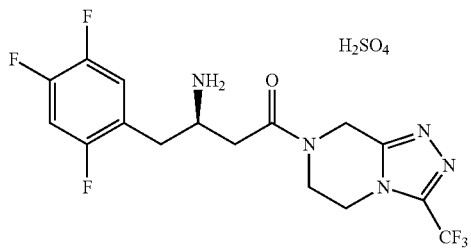

Sitagliptin sulfate (1:1)

which is characterized by having an X-ray powder diffraction pattern having peaks at 2θ values equal to 14.8±0.2°, 15.1±0.2°, 17.1±0.2°, 19.4±0.2°, 21.9±0.2°, 24.0±0.2° and 25.4±0.2°, and by having a DSC with an endothermic signal at approximately 216° C.

One aspect of the present invention also provides a process for obtaining the novel crystalline form of the addition salt of sitagliptin with sulfuric acid (1:1) that can be readily industrialized.

Another aspect of the invention provides a pharmaceutical composition comprising a pharmaceutically effective amount of the novel crystalline form of the addition salt of sitagliptin with sulfuric acid (1:1), as well as a method for treating type 2 diabetes which comprises administering a formulation comprising said pharmaceutical composition to patients.

DETAILED DESCRIPTION OF CERTAIN EMBODIMENTS OF THE INVENTION

Figure 1:
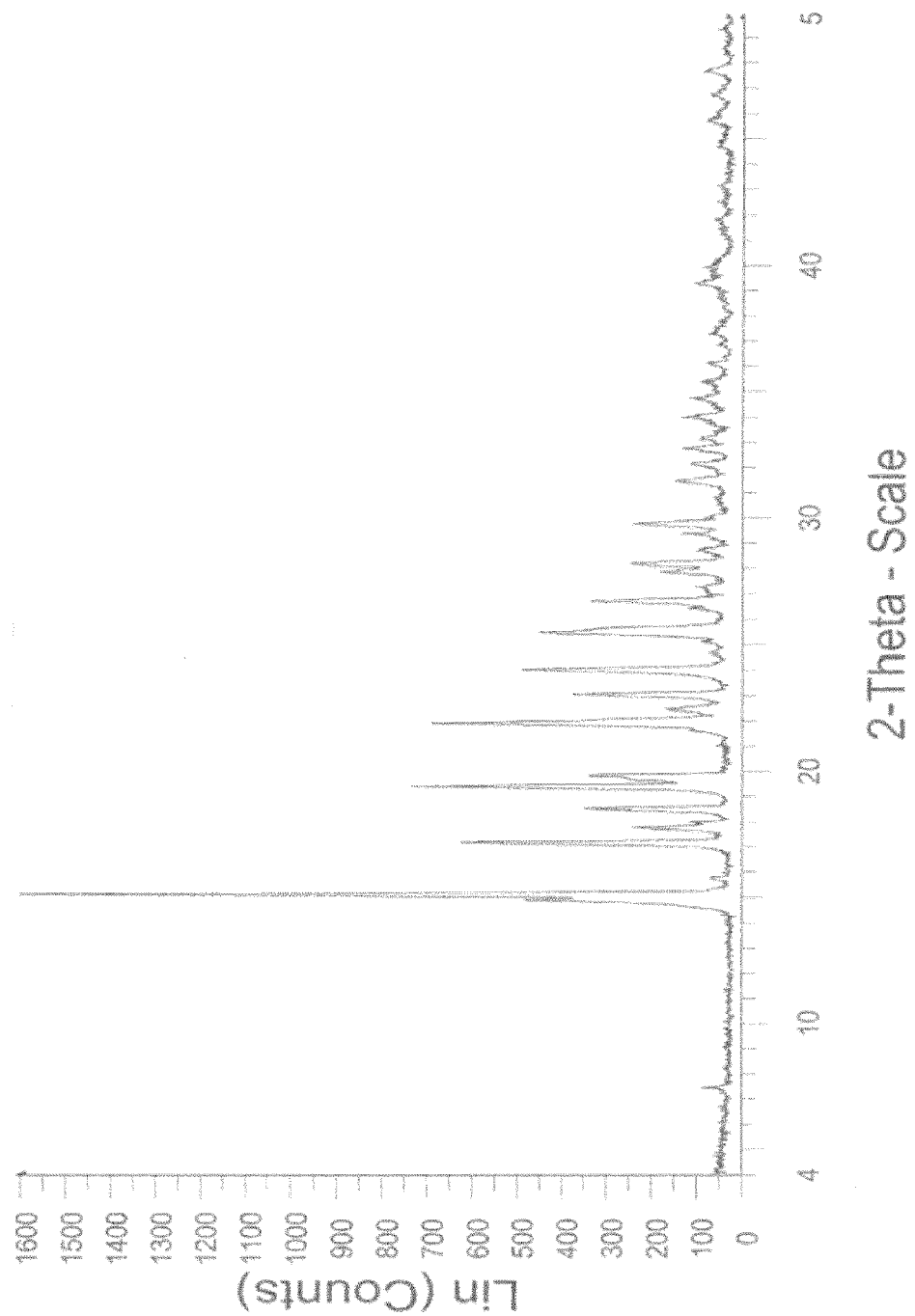
FIG. 1 shows an XRPD pattern obtained for the product of Example 1.

The present invention relates to a novel crystalline form, called form M, of the addition salt of sitagliptin with sulfuric acid (1:1) having an unexpected stability in terms of its hygroscopicity characteristics. In the present invention the terms addition salt of sitagliptin with sulfuric acid (1:1) and sitagliptin sulfate are used interchangeably to designate the salt formed by one mole of sitagliptin and one mole of sulfuric acid.

The crystalline form obtained has a percentage of water of less than 0.05% determined by thermal gravimetric analysis (TGA) (under the conditions described in the experimental part) and it was found to be non-hygroscopic under the conditions of the European Pharmacopeia Ed. 6.0 Section 5.11, i.e., the degree of hydration at 80% relative humidity and at a temperature of 25° C. is less than 0.2%; nor is the crystalline form hygroscopic at 97% relative humidity and at a temperature of 25° C.

The crystalline form was characterized by means of XRPD and DSC under the conditions described in the experimental part. The characterization by means of XRPD shows a highly crystalline state, unlike what was observed in virtually all the crystalline forms of sitagliptin sulfate salt described above. This is shown in an XRPD pattern with a number of well defined peaks. The novel crystalline form, called form M, of the addition salt of sitagliptin with sulfuric acid (1:1) has a pattern having peaks at 2θ values equal to 14.8±0.2°, 15.1±0.2°, 17.1±0.2°, 19.4±0.2°, 21.9±0.2°, 24.0±0.2° and 25.4±0.2°, and more preferably also having peaks at 2θ values equal to 18.5±0.2°, 19.8±0.2°, 23.0±0.2° and 26.7±0.2°.

Analysis by means of DSC gives a melting endotherm at 216.0±1.0° C. Said value is the highest value out of those described in the literature for the crystalline forms of sulfate salt and for any other pharmaceutically acceptable salt of sitagliptin other than the marketed phosphate salt and tosylate salt (described in WO2005/072530A) and dodecyl sulfate salt (described in WO2007/035198A).

Another aspect of the present invention is a process for obtaining the novel crystalline form from sitagliptin base. This process comprises reacting a sulfuric acid solution with a sitagliptin base solution or suspension (preferably a solution) in a mixture of water and one or more water-miscible organic solvents. Water-miscible organic solvent is understood as an organic compound, liquid at 10° C., which can be mixed with water in any proportion to form a solution.

In a preferred embodiment of the present invention, the ratio of volume (in ml) of organic solvent to weight (in g) of sitagliptin base is between 10:1 and 30:1 and the ratio of volume (in ml) of water to weight (in g) of sitagliptin base is between 1:1 and 5:1, more preferably the ratio of volume (in ml) of organic solvent to weight (in g) of sitagliptin base is between 15:1 and 20:1 and the ratio of volume (in ml) of water to weight (in g) of sitagliptin base is between 1:1 and 3:1. Volume of organic solvent includes both the volume used for dissolving or suspending the sitagliptin base and that which is added together with the sulfuric acid.

In one embodiment of the invention, the sulfuric acid solution is added to the sitagliptin base suspension or solution at a ratio comprised between 0.9:1 and 1.1:1 moles of $H_2SO_4$ per mol of sitagliptin base.

In one embodiment of the present invention, the sulfuric acid is a sulfuric acid solution with a concentration greater than 40%, preferably greater than 50%, more preferably greater than 75%, more preferably greater than 95% and still more preferably greater than 98%, for example 98.1%.

In another embodiment of the present invention, the water-miscible organic solvent/solvents is/are selected from solvents which are capable of dissolving at least 1 g of sitagliptin sulfate per 10 ml of solvent at a temperature of 25° C. when mixed with 1 ml of water, or in other words, a mixture of 10 ml of said solvent/solvents and 1 ml of water is capable of dissolving at least 1 g of sitagliptin sulfate at a temperature of 25° C.

In another embodiment of the present invention, the water-miscible organic solvent/solvents is/are selected from the group consisting of acetone and aliphatic alcohols with 1 to 5 carbon atoms, such as methanol, ethanol, n-propanol, isopropanol, n-butanol, isobutanol, sec-butanol, tert-butanol, 1-pentanol, 3-methyl-1-butanol, 2-methyl-1-butanol, 2,2-dimethyl-1-propanol, 3-pentanol, 2-pentanol, 3-methyl-2-butanol and 2-methyl-2-butanol, preferably 2-propanol and ethanol, more preferably ethanol.

In another embodiment of the present invention, the production process described above can comprise using crystals obtained previously from the novel crystalline form object of the present invention. It is believed that said crystals act as crystallization nuclei facilitating product crystallization.

Sitagliptin base can be easily obtained from the known starting compounds (3R)-3-tert-butoxycarbonylamino-4-(2,4,5-trifluorophenyl)-butyric acid and 3-(trifluoromethyl)-5,6,7,8-tetrahydro-[1,2,4]triazolo[4,3-a]pyrazine, as described in document WO 2009/064476 A1, using a method based on the documents by Merck & Co. WO 2003/004498 A2 or Journal Medicinal Chemistry, 2005, 48(1), 141-151.

The condensation of both mentioned compounds yields the corresponding N-protected intermediate. The acid hydrolysis of the tert-butoxycarbonyl protecting group allows finally obtaining sitagliptin base as a white solid with a melting point of 115° C., coinciding with that described above in the literature (WO 2004/085378 A2).

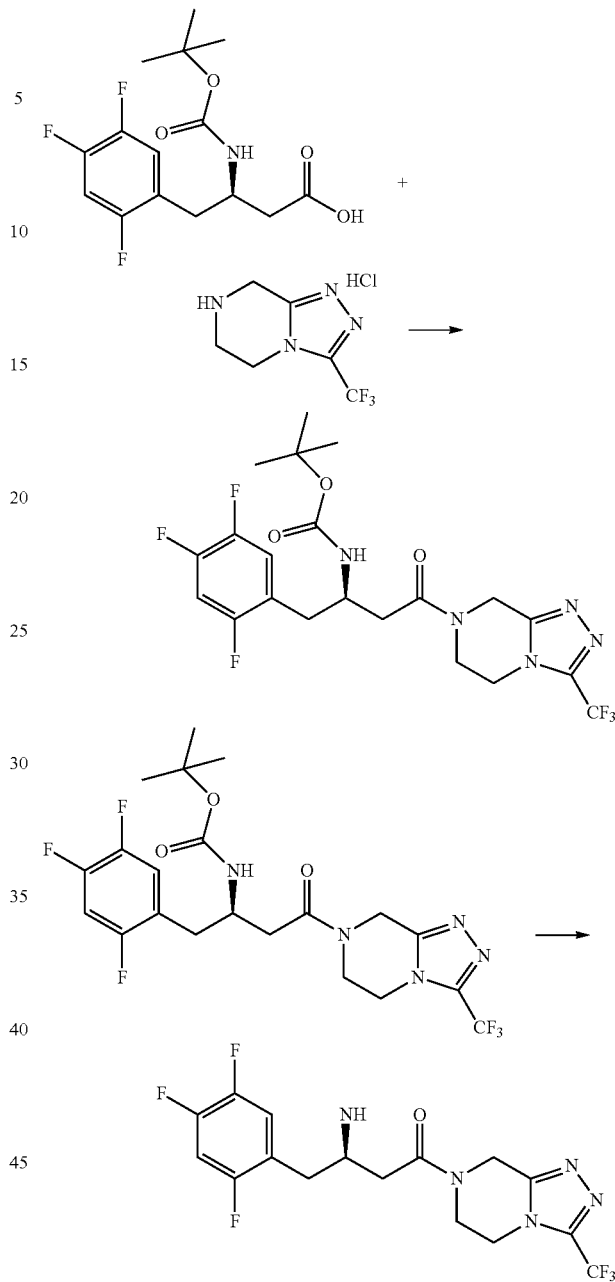

In another embodiment of the present invention, the crystalline form of the invention can be obtained by means of crystallizing sitagliptin sulfate (1:1) of a mixture of water and one or more water-miscible organic solvents. The starting product used can be sitagliptin sulfate in an amorphous form or in any crystalline form. In a preferred embodiment of the present invention, the ratio of volume (in ml) of organic solvent to weight (in g) of sitagliptin sulfate is between 10:1 and 30:1 and the ratio of volume (in ml) of water to weight (in g) of sitagliptin sulfate is between 1:1 and 5:1, more preferably the ratio of volume (in ml) of organic solvent to weight (in g) of sitagliptin sulfate is between 15:1 and 20:1 and the ratio of volume (in ml) of water to weight (in g) of sitagliptin sulfate is between 1:1 and 3:1.

In another embodiment of the present invention, the water-miscible solvent is selected from acetone and aliphatic alcohols with 1 to 5 carbon atoms, such as methanol, ethanol, n-propanol, isopropanol, n-butanol, isobutanol, sec-butanol, tert-butanol, 1-pentanol, 3-methyl-1-butanol, 2-methyl-1-butanol, 2,2-dimethyl-1-propanol, 3-pentanol, 2-pentanol, 3-methyl-2-butanol and 2-methyl-2-butanol, preferably 2-propanol and ethanol, more preferably ethanol.

In another embodiment of the present invention, the production process from sitagliptin sulfate described above can comprise using crystals obtained previously from the novel crystalline form object of the present invention. It is believed that said crystals act as crystallization nuclei facilitating product crystallization.

The presence of water in the medium is necessary for obtaining the crystalline form of the invention. All the tests performed from sitagliptin base in a water-free organic solvent or mixture of organic solvents led to the production of sitagliptin sulfate that does not coincide with the crystalline form of the invention.

Another aspect of the present invention is the pharmaceutical compositions comprising the crystalline form of sitagliptin sulfate object of the present invention and at least one pharmaceutically acceptable excipient.

In a preferred embodiment, the pharmaceutical composition according to the present invention comprises:
from 1% to 80% by weight, with respect to the total weight of the composition, of sitagliptin sulfate of the invention;
from 0% to 99% by weight, with respect to the total weight of the composition, of one or more diluents/fillers;
from 0% to 20% by weight, with respect to the total weight of the composition, of one or more disintegrants;
from 0% to 20% by weight, with respect to the total weight of the composition, of one or more glidants and/or lubricants; and
optionally a film coat; with the proviso that at least one pharmaceutically acceptable excipient selected from the group consisting of diluents/fillers, disintegrants, glidants and lubricants, is present in the composition.

In a more preferred embodiment, the pharmaceutical composition according to the present invention comprises:
from 10% to 50% by weight, with respect to the total weight of the composition, of sitagliptin sulfate of the invention;
from 40% to 80% by weight, with respect to the total weight of the composition, of one or more diluents/fillers;
from 0% to 10% by weight, preferably from 0.1% to 10% by weight, with respect to the total weight of the composition, of one or more disintegrants;
from 0% to 10% by weight, preferably from 0.1% to 10% by weight, with respect to the total weight of the composition, of one or more glidants and/or lubricants; and
optionally a film coat.

In a more preferred embodiment, the pharmaceutical composition according to the present invention comprises:
from 20% to 40% by weight, with respect to the total weight of the composition, of sitagliptin sulfate of the invention;
from 50% to 70% by weight, with respect to the total weight of the composition, of one or more diluents/fillers;
from 1% to 6% by weight with respect to the total weight of the composition, of one or more disintegrants;
from 1% to 6% by weight with respect to the total weight of the composition, of one or more glidants and/or lubricants; and
optionally a film coat.

The excipients are well-known to the skilled person, e.g. from Remington, The Science and Practice Of Pharmacy, 22$^{nd}$ Edition, 2012, which is incorporated herein by reference in regard to pharmaceutical excipients, particularly volume 1: "The Science of Pharmacy", pages 1049-1070.

Excipients that can be used in the pharmaceutical composition of the present invention include, but are not limited to:
antioxidants like butylated hydroxyanisole and butylated hydroxytoluene,
binders like starch and derivatives thereof, cellulose and derivatives thereof, carboxymethyl cellulose sodium (CMC), guar gum, lactose, povidone, tragacanth, zein,
colors and pigments,
diluents/fillers, like calcium carbonate, calcium sulfate, calcium hydrogenphosphate anhydrous, microcrystalline cellulose (MCC), powdered cellulose, dextrates, dextrose, dextrin, kaolin, lactose, maltodextrin, starch, mannitol, sorbitol, sucrose, lactose, isomalt, preferably microcrystalline cellulose, calcium hydrogenphosphate anhydrous, mannitol, lactose, sorbitol and isomalt,
disintegrants like croscarmellose sodium, crospovidone, guar gum, sodium starch glycolate, preferably croscarmellose sodium and crospovidone,
emollients like glycerin, glyceryl monostearate, isopropyl myristate, polyethylene glycols,
emulsifiers like carbomer, carrageenan, lanolin, lecithin, mineral oil, pectin, sorbitan esters,
flavors,
glidants/antiadherents like talc or colloidal silicon dioxide, preferably colloidal silicon dioxide,
lubricants like calcium stearate, magnesium stearate, sodium stearyl fumarate, stearic acid, preferably sodium stearyl fumarate and magnesium stearate,
plasticizers like triethanolamine,
preservatives like alcohol or sorbic acid,
surfactants like polyethylene glycols, sodium lauryl sulfate, and
suspending agents like acacia, agar.

Some of the excipients cited above have sweetening properties, such as sorbitol, sucrose, dextrose, and mannitol. However, sweeteners may also be added to the pharmaceutical compositions of the invention, like fructose and xylitol.

The pharmaceutical composition of the invention may also be coated with coating agents like hypromellose (HPMC), carboxymethyl cellulose sodium (CMC), carnauba wax, cellulose acetate phthalate, gelatin, hydroxypropyl cellulose (HPC), maltodextrin, methylcellulose, poly(meth)acrylates, polyvinyl alcohol (PVA), or commercially coating agents, as used in the examples.

Also further excipients can be used. Suitable excipients are also known from e.g. WO 2005/067976, which is incorporated hereby in regard to excipients.

The pharmaceutical compositions of the invention include compositions suitable for being administered orally, subcutaneously, parenterally, locally (ointments, creams, powders), in the form of droplets, as a nasal or mouth spray. The person skilled in the formulation of pharmaceutical products knows how to formulate compositions object of the present invention other than the compositions described above. The pharmaceutical composition of the present invention is preferably provided in the form of an oral dosage form. The oral dosage form can be thereby a solid oral dosage form, like powders, granules, pellets, tablets and capsules, or a liquid oral dosage form, like syrups, dispersions and emulsions. Preferably, the pharmaceutical formulation is provided in the form of a solid oral dosage form. Examples of solid oral dosage forms are known to the skilled person from e.g. Remington, The Science and Practice of Pharmacy, 2$^{nd}$ edition, 2012, volume 1: The Science of Pharmacy, pages 947-976.

Preferably the solid dosage form is in the form of a tablet, coated tablet, capsule, pill, powder or granule. The formulations can be adapted for immediate release, delayed release or modified release of the active ingredient.

It is possible that the solid oral dosage form is uncoated or coated, e.g. film coated, powder coated, enteric coated, sugar coated or modified release coated. Suitable substances for coating are known to the skilled person.

Methods of preparing the solid oral dosage forms are known to the skilled person. Preferable methods for preparing tablets are direct compression and dry and wet granulation (e.g. high shear or fluid bed).

Preferred as solid oral dosage form are tablets and coated tablets as the pharmaceutical formulation of the present invention can be easily subjected to direct compression.

In one embodiment of the present invention, the pharmaceutical composition is a solid at a temperature of 25° C.

In another embodiment of the present invention, the pharmaceutical compositions comprising the crystalline form of sitagliptin sulfate object of the present invention further comprise metformin.

In another embodiment of the present invention, the pharmaceutical compositions comprising the crystalline form of sitagliptin sulfate object of the present invention further comprise a sulfonylurea selected from the group consisting of tolbutamide, acetohexamide, tolazamide, chlorpropamide, glipizide, glyburide, glimepiride and gliclazide, preferably glimepiride.

In another embodiment of the present invention, the pharmaceutical compositions comprising the crystalline form of sitagliptin sulfate object of the present invention further comprise a peroxisome proliferator-activated receptor gamma (PPARγ) agonist selected from the group consisting of rosiglitazone, pioglitazone and troglitazone, preferably pioglitazone.

In another embodiment of the present invention, the pharmaceutical compositions comprising the crystalline form of sitagliptin sulfate object of the present invention further comprise a 3-hydroxy-3-methyl-glutaryl-coenzyme A reductase (HMG-CoA reductase) inhibitor selected from the group consisting of lovastatin, simvastatin, pravastatin, fluvastatin, atorvastatin, rivastatin, itavastatin and rosuvastatin, preferably simvastatin.

Another aspect of the present invention is crystalline form of sitagliptin sulfate object of the present invention for use as a medicament.

In one embodiment of the present invention, the crystalline form of sitagliptin sulfate object of the present invention is for use in the improvement of blood glucose control in type 2 diabetes mellitus patients.

Another aspect of the present invention is the crystalline form of sitagliptin sulfate of the present invention in combination with metformin for use in the improvement of blood glucose control in type 2 diabetes mellitus patients.

One embodiment of the present invention is the crystalline form of sitagliptin sulfate object of the present invention is in combination with a sulfonylurea selected from the group consisting of tolbutamide, acetohexamide, tolazamide, chlorpropamide, glipizide, glyburide, glimepiride and gliclazide, preferably glimepiride, for use in the improvement of blood glucose control in type 2 diabetes mellitus patients.

Another embodiment of the present invention is the crystalline form of sitagliptin sulfate object of the present invention in combination with a peroxisome proliferator-activated receptor gamma (PPARγ) agonist selected from the group consisting of rosiglitazone, pioglitazone and troglitazone, preferably pioglitazone, for use in the improvement of blood glucose control in type 2 diabetes mellitus patients.

Another embodiment of the present invention is the crystalline form of sitagliptin sulfate object of the present invention is in combination with a 3-hydroxy-3-methyl-glutaryl-coenzyme A reductase (HMG-CoA reductase) inhibitor selected from the group consisting of lovastatin, simvastatin, pravastatin, fluvastatin, atorvastatin, rivastatin, itavastatin and rosuvastatin, preferably simvastatin, for use in the improvement of blood glucose control in type 2 diabetes mellitus patients.

Another aspect of the present invention is the use of the crystalline form of sitagliptin sulfate object of the present invention for the manufacture of a medicament.

In one embodiment of the present invention, the use of the crystalline form of sitagliptin sulfate object of the present invention is for the manufacture of a medicament to improve blood glucose control in type 2 diabetes mellitus patients.

Another aspect of the present invention is the use of the crystalline form of sitagliptin sulfate of the present invention in combination with metformin for the manufacture of a medicament to improve blood glucose control in type 2 diabetes mellitus patients.

In one embodiment of the present invention, the use of the crystalline form of sitagliptin sulfate object of the present invention is in combination with a sulfonylurea selected from the group consisting of tolbutamide, acetohexamide, tolazamide, chlorpropamide, glipizide, glyburide, glimepiride and gliclazide, preferably glimepiride, for the manufacture of a medicament to improve blood glucose control in type 2 diabetes mellitus patients.

In another embodiment of the present invention, the use of the crystalline form of sitagliptin sulfate object of the present invention is in combination with a peroxisome proliferator-activated receptor gamma (PPARγ) agonist selected from the group consisting of rosiglitazone, pioglitazone and troglitazone, preferably pioglitazone, for the manufacture of a medicament to improve blood glucose control in type 2 diabetes mellitus patients.

In one embodiment of the present invention, the use of the crystalline form of sitagliptin sulfate object of the present invention is in combination with a 3-hydroxy-3-methyl-glutaryl-coenzyme A reductase (HMG-CoA reductase) inhibitor selected from the group consisting of lovastatin, simvastatin, pravastatin, fluvastatin, atorvastatin, rivastatin, itavastatin and rosuvastatin, preferably simvastatin, for the manufacture of a medicament to improve blood glucose control in type 2 diabetes mellitus patients.

Another aspect of the present invention, is a method for improving the of blood glucose control in type 2 diabetes mellitus patients which comprised administering a crystalline form of sitagliptin sulfate object of the present invention.

Another aspect of the present invention is a method for improving the of blood glucose control in type 2 diabetes mellitus patients which comprises administering the crystalline form of sitagliptin sulfate of the present invention in combination with metformin.

One embodiment of the present invention is a method for improving the of blood glucose control in type 2 diabetes mellitus patients which comprises administering the crystalline form of sitagliptin sulfate object of the present invention is in combination with a sulfonylurea selected from the group consisting of tolbutamide, acetohexamide, tolazamide, chlorpropamide, glipizide, glyburide, glimepiride and gliclazide, preferably glimepiride.

Another embodiment of the present invention is a method for improving the of blood glucose control in type 2 diabetes mellitus patients which comprises administering the crystalline form of sitagliptin sulfate object of the present invention in combination with a peroxisome proliferator-activated receptor gamma (PPARγ) agonist selected from the group consisting of rosiglitazone, pioglitazone and troglitazone, preferably pioglitazone.

Another embodiment of the present invention is a method for improving the of blood glucose control in type 2 diabetes mellitus patients which comprises administering the crystalline form of sitagliptin sulfate object of the present invention is in combination with a 3-hydroxy-3-methyl-glutaryl-coenzyme A reductase (HMG-CoA reductase) inhibitor selected from the group consisting of lovastatin, simvastatin, pravastatin, fluvastatin, atorvastatin, rivastatin, itavastatin and rosuvastatin, preferably simvastatin.

EXAMPLES

The following abbreviations have been used in the experimental part:

HPLC: High Performance Liquid Chromatography
DSC: Differential Scanning calorimetry
XRPD: X-Ray Powder Diffraction
TGA: Thermal Gravim etric Analysis
PSD: Particle Size Distribution Methods of Analysis XRPD and DSC The crystalline form obtained by means of the described examples is identified by means of its X-ray diffraction (XRPD) and differential scanning calorimetry (DSC) patterns.

The XRPD analyses were performed in a Siemens model D-500 X-ray powder diffractometer equipped with a copper anode. Scan parameters: 4-50 2θ degrees, continuous scanning, ratio: 1.2 degrees/minute.

DSC analyses were performed in a Mettler Toledo 822e apparatus with STARe SW8.01 software. Parameters: heating range from 25 to 250° C. with a 10° C./min ramp and a 50 ml/min $N_2$ flow. The measurement is taken with a perforated sealed capsule.

TGA

TGA analyses were performed using a Mettler/Toledo TGA/SDTA851e thermobalance. Parameters: heating range from 30 to 300° C. with a 10° C./min ramp and a 50 ml/min dry $N_2$ flow.

HPLC

The analysis is performed in a Waters Alliance 2690 Mod. chromatograph with a 2487 dual wavelength UV detector, equipped with a 5 μm×0.46 cm octadecylsilyl column. Parameters: flow rate 0.7 ml/minute, temperature 30° C., detection at 210 nm, injection volume 10 μl and analysis time 35 minutes.

PSD

The analysis is performed in a Sympatec Helos laser diffraction particle analyzer no. 1054. The processor used is Windox 5.4.0.0 HRLD and the measurement is made with a R3 lens (measurement range: 0.9 to 175 mm) at a pressure of 1.5 bar. The measurement provides the values D10, D50 and D90 representing the measurement below which 10%, 50% and 90% of the particles of the product on which the measurement was taken are found, respectively.

Water Content (Karl-Fisher Method)

The analysis is performed in a Mettler Toledo W30. It is determined in 0.2 g of sample using Hydranal medium K as solvent and Hydranal composite 5K as titrant.

Example 1

Figure 7:
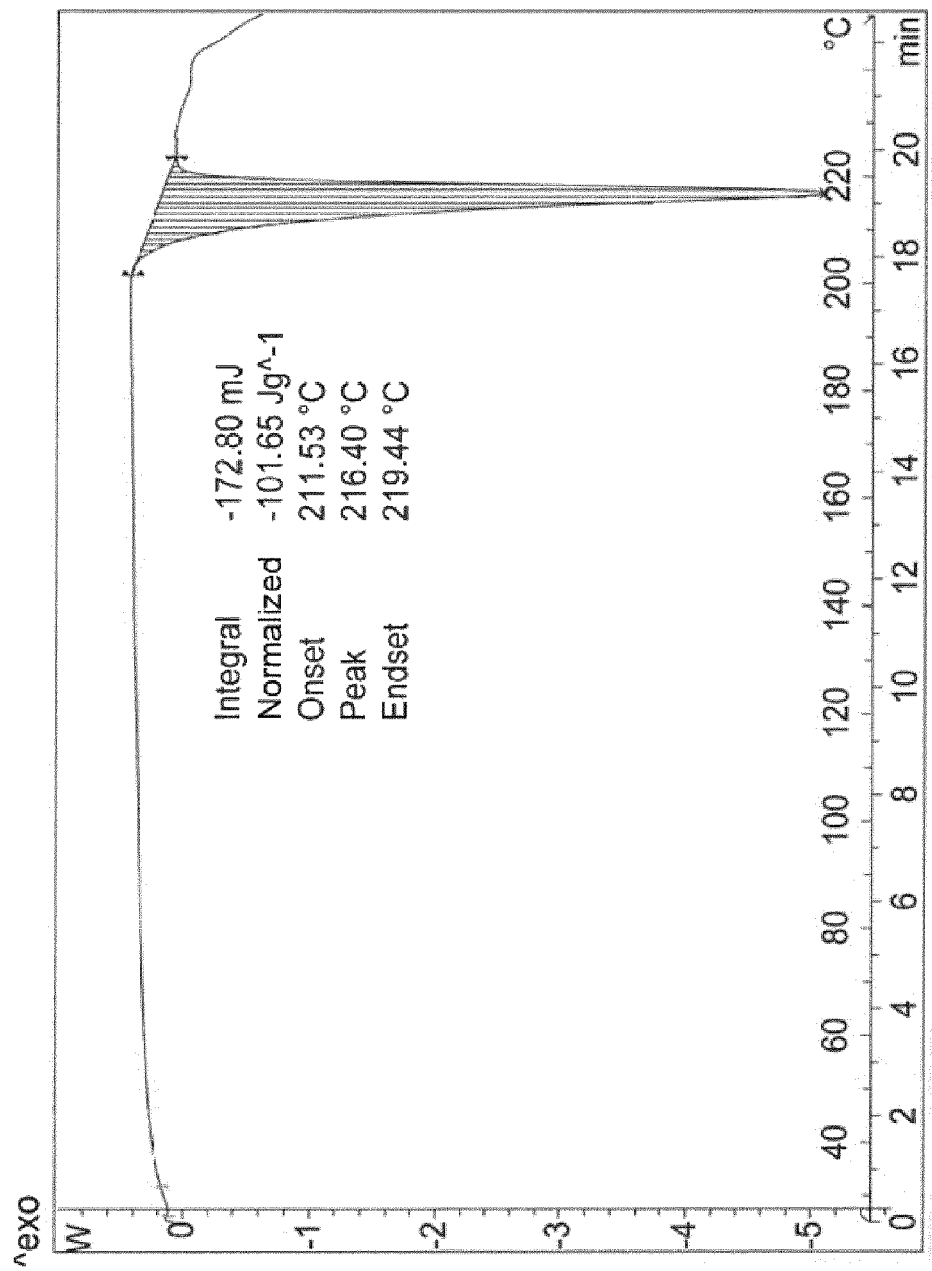
FIG. 7 shows a DSC pattern obtained for the product of Example 1.
Figure 12:
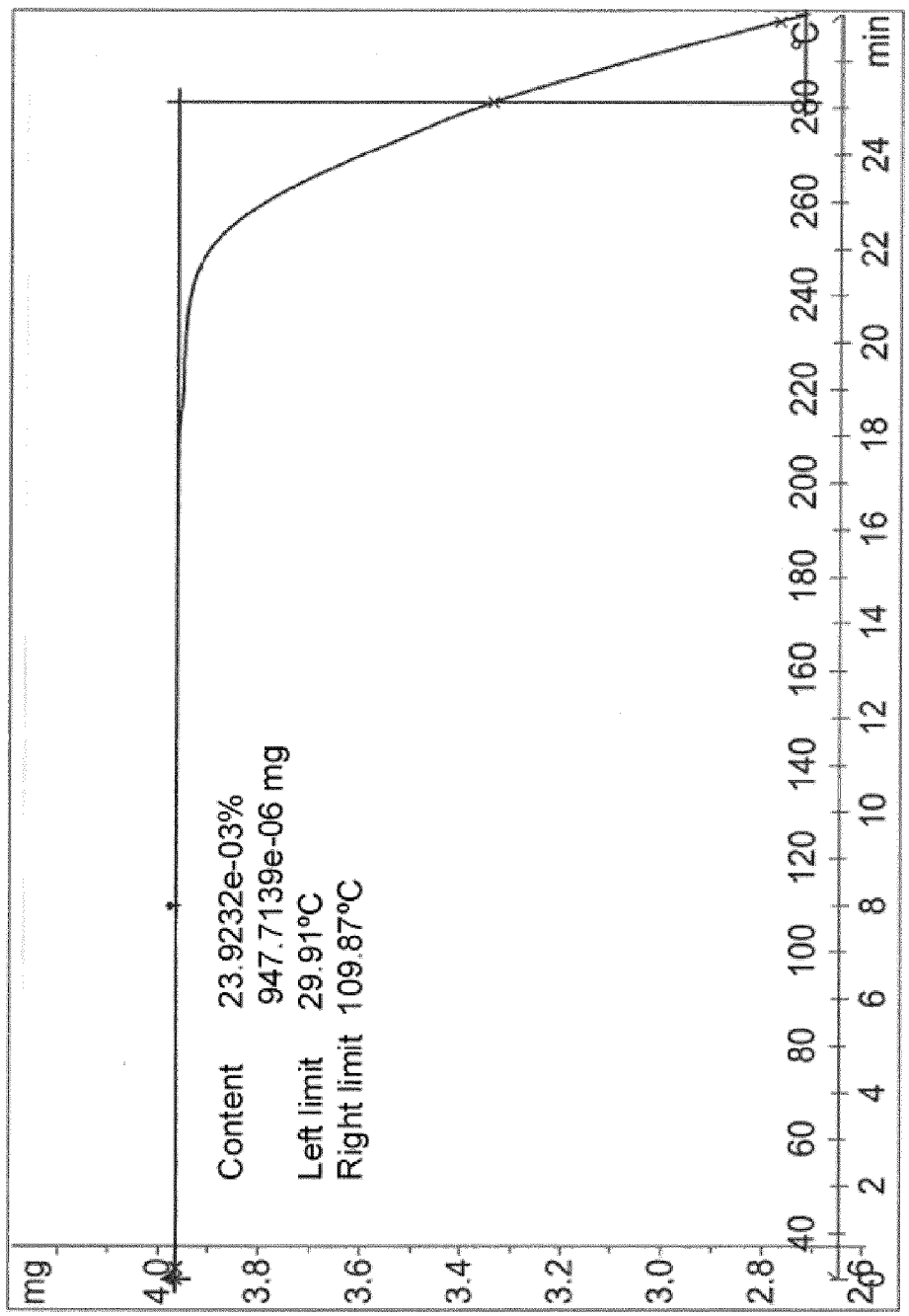
FIG. 12 shows a TGA pattern obtained for the product of Example 1.

25.0 g of sitagliptin base (61.3 mmoles) were dissolved at 25-26° C. in a mixture of 190 ml of absolute ethanol and 30 ml of water. A previously prepared solution of 98.1% $H_2SO_4$ (6.2 g, 62.01 mmoles) in ethanol (190 ml) was slowly added to said solution, maintaining the temperature between 20-25° C. 27.5 ml of water were then added to the obtained mixture and it was heated to approximately 50° C. The resulting solution was slowly cooled to the approximate temperature of 25° C., the appearance of a white precipitate being observed. It was maintained for 4 hours at said temperature. The solid obtained was filtered and washed in the filter with absolute ethanol (3×25 ml). The wet product was dried in a vacuum oven at 40° C. for 20 hours to yield 22.0 g (43.5 mmoles) of a white crystalline solid (71.0%). The product thus obtained has an XRPD pattern corresponding to form M of sitagliptin sulfate (FIG. 1). The DSC of the product (FIG. 7) shows an endothermic signal at 216.4° C. and the water content determined by TGA (FIG. 12) is 0.02%.

The crystalline salt thus obtained can be purified if necessary by means of any of the methods described in Examples 3-5.

Example 2

Figure 2:
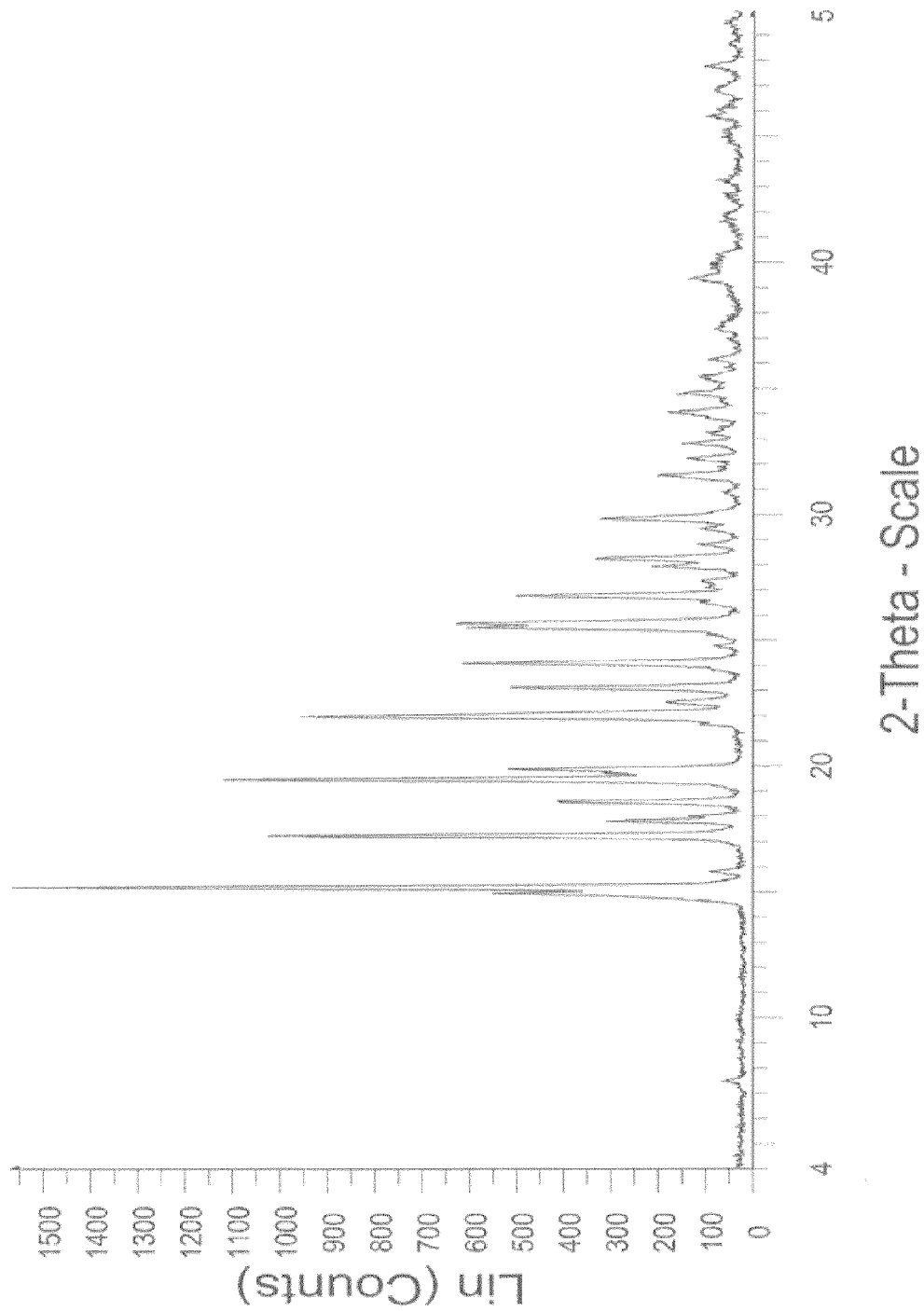
FIG. 2 shows an XRPD pattern obtained for the product of Example 2.
Figure 3:
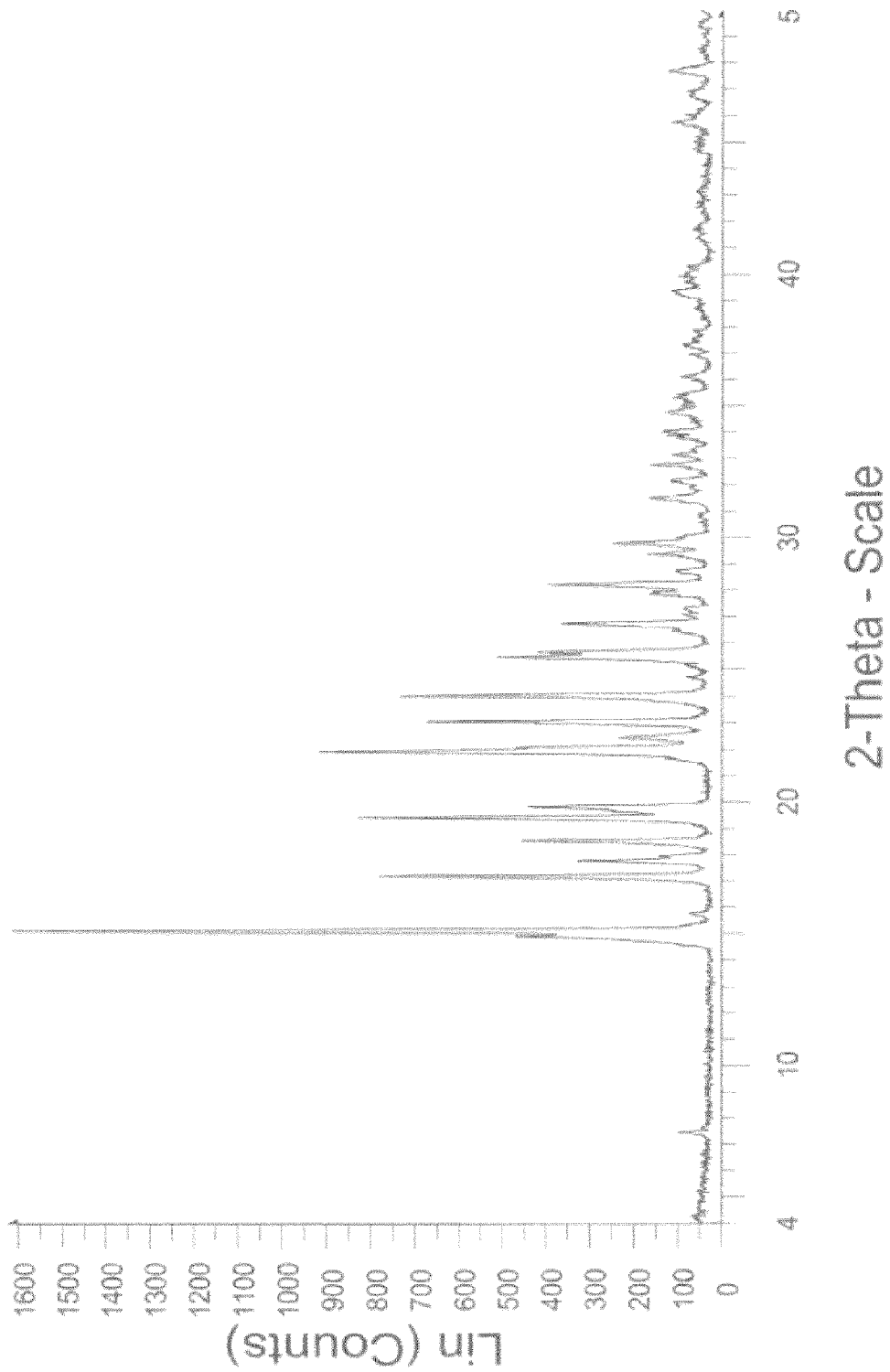
FIG. 3 shows an XRPD pattern obtained for the product of Example 2 (wet).
Figure 8:
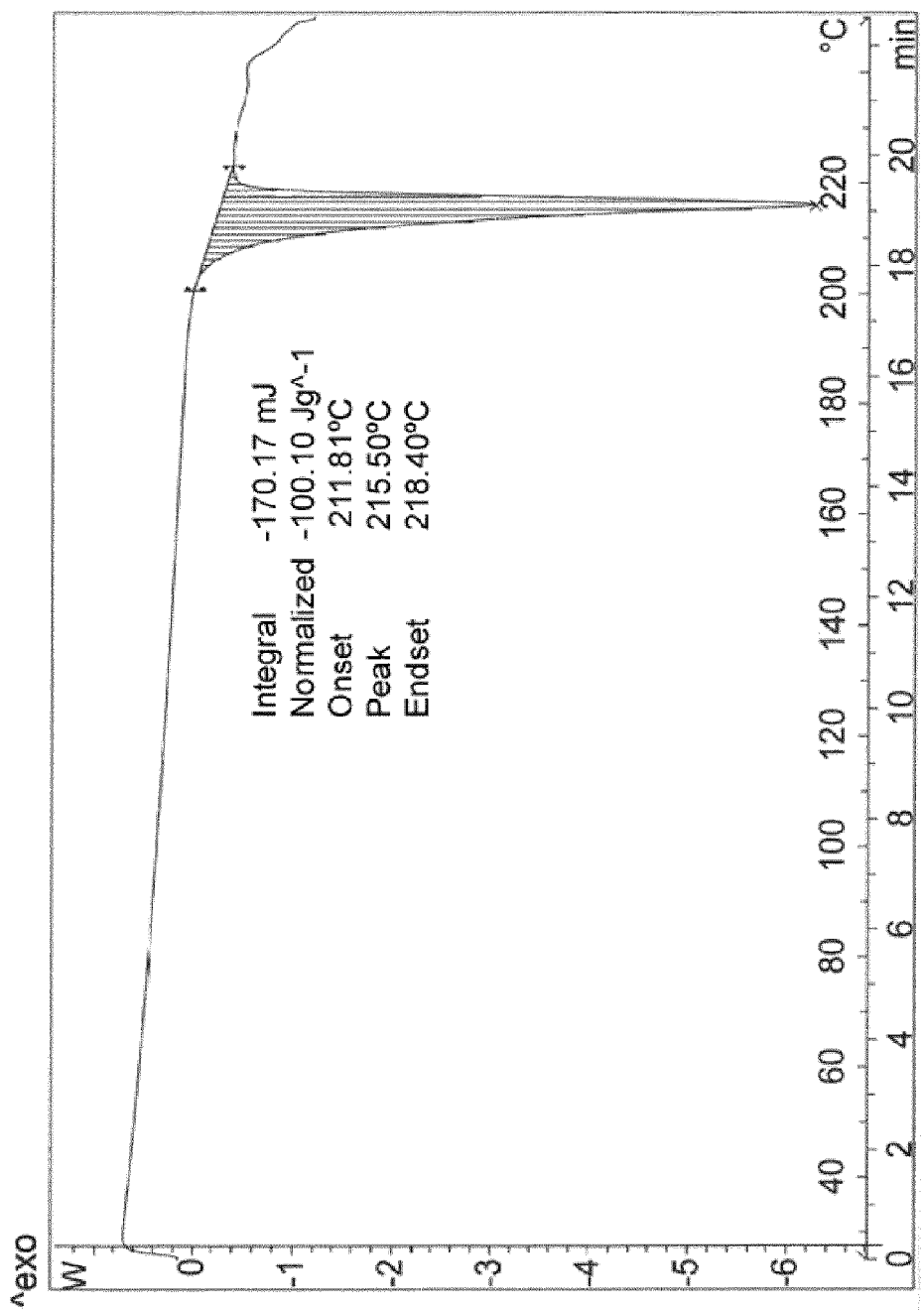
FIG. 8 shows a DSC pattern obtained for the product of Example 2.
Figure 9:
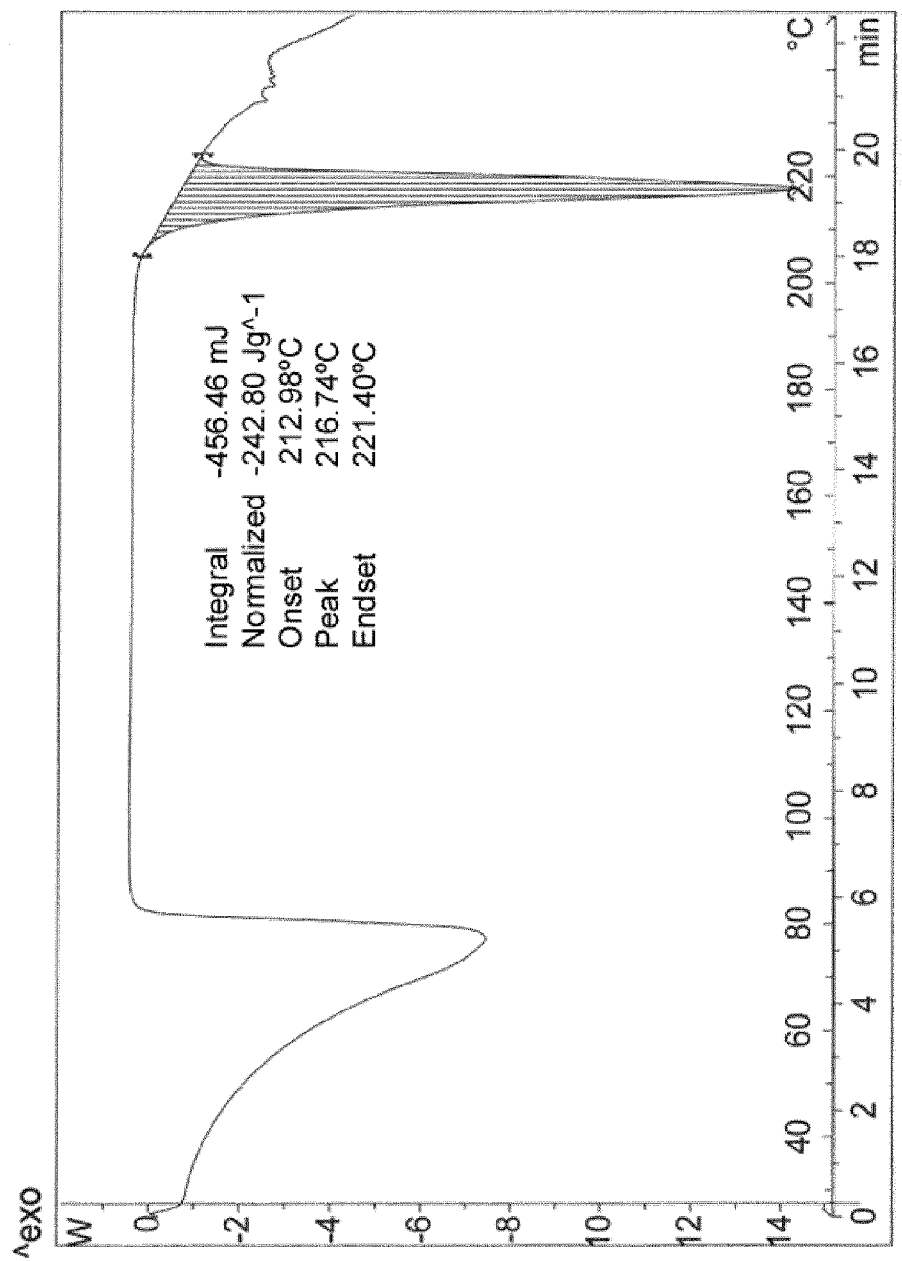
FIG. 9 shows a DSC pattern obtained for the product of Example 2 (wet).
Figure 13:
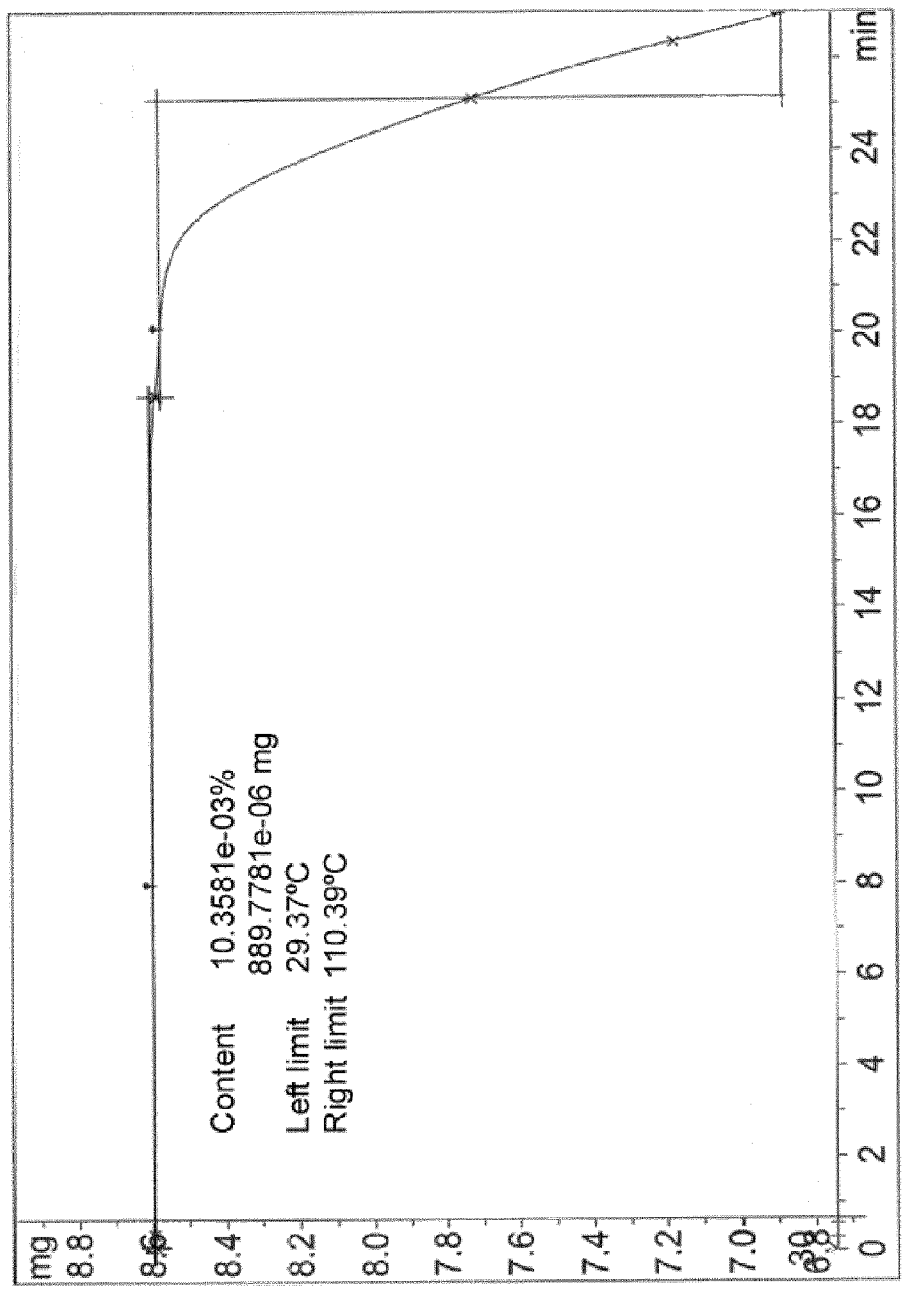
FIG. 13 shows a TGA pattern obtained for the product of Example 2.

100.0 g (245.5 mmoles) of sitagliptin base were dissolved at 20-22° C. in a mixture of 750 ml of absolute ethanol and 120 ml of water. A previously prepared solution of 98.1% $H_2SO_4$ (24.9 g, 240.9 mmoles) in ethanol (760 ml) was slowly added to said solution, maintaining the temperature between 20-25° C. When approximately ⅔ of the total volume of the acid solution had been added, the addition was stopped and 1.0 g (1.978 mmoles) of crystalline form M of sitagliptin sulfate obtained by means of any of the processes described in Examples 1 and 3-5 was added to the reaction mixture. The presence of a white precipitate that remains undissolved was immediately noticed. The addition of the acid solution was continued and once this ended, the mixture obtained was maintained at a temperature of 20-25° C. for 4 hours. The solid obtained was filtered and washed in the filter with absolute ethanol (2×100 ml). The wet product was dried in a vacuum oven at 40° C. for 22 hours to yield 97.1 g (192.1 mmoles) of a white crystalline solid (77.6%). XRPDs both of the wet product (FIG. 3) and of the dry product (FIG. 2) which correspond with form M of sitagliptin sulfate were performed. The DSC of the wet product (FIG. 9) shows an endothermic signal at 216.7° C. whereas the dry product showed an endothermic signal at 215.5° C. (FIG. 8). The water content determined by TGA (FIG. 13) is 0.02%. The product thus obtained had a particle size distribution (PSD) corresponding to D90: 254.21 μm, D50: 141.64 μm, D10: 5.32 μm. By adjusting the grinding conditions a product with a particle size distribution (PSD) corresponding to D90 120.84 μm, D50: 6.01 μm, D10: 1.50 μm could be obtained and it was found that the ground product is still the crystalline form of sitagliptin sulfate object of the present invention.

The crystalline salt thus obtained can be purified if necessary by means of any of the methods described in Examples 3-5.

Example 3

Figure 4:
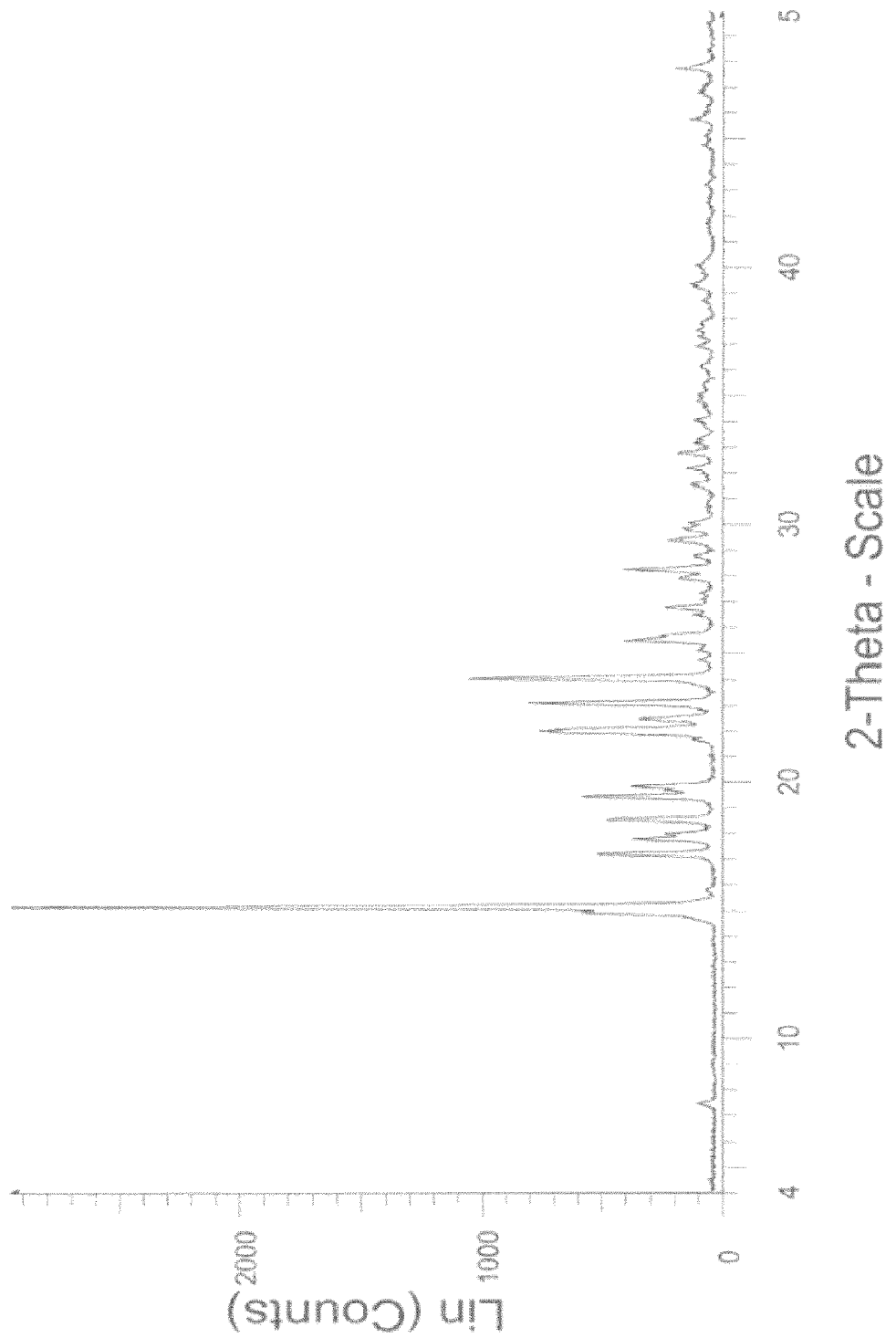
FIG. 4 shows an XRPD pattern obtained for the product of Example 3.
Figure 10:
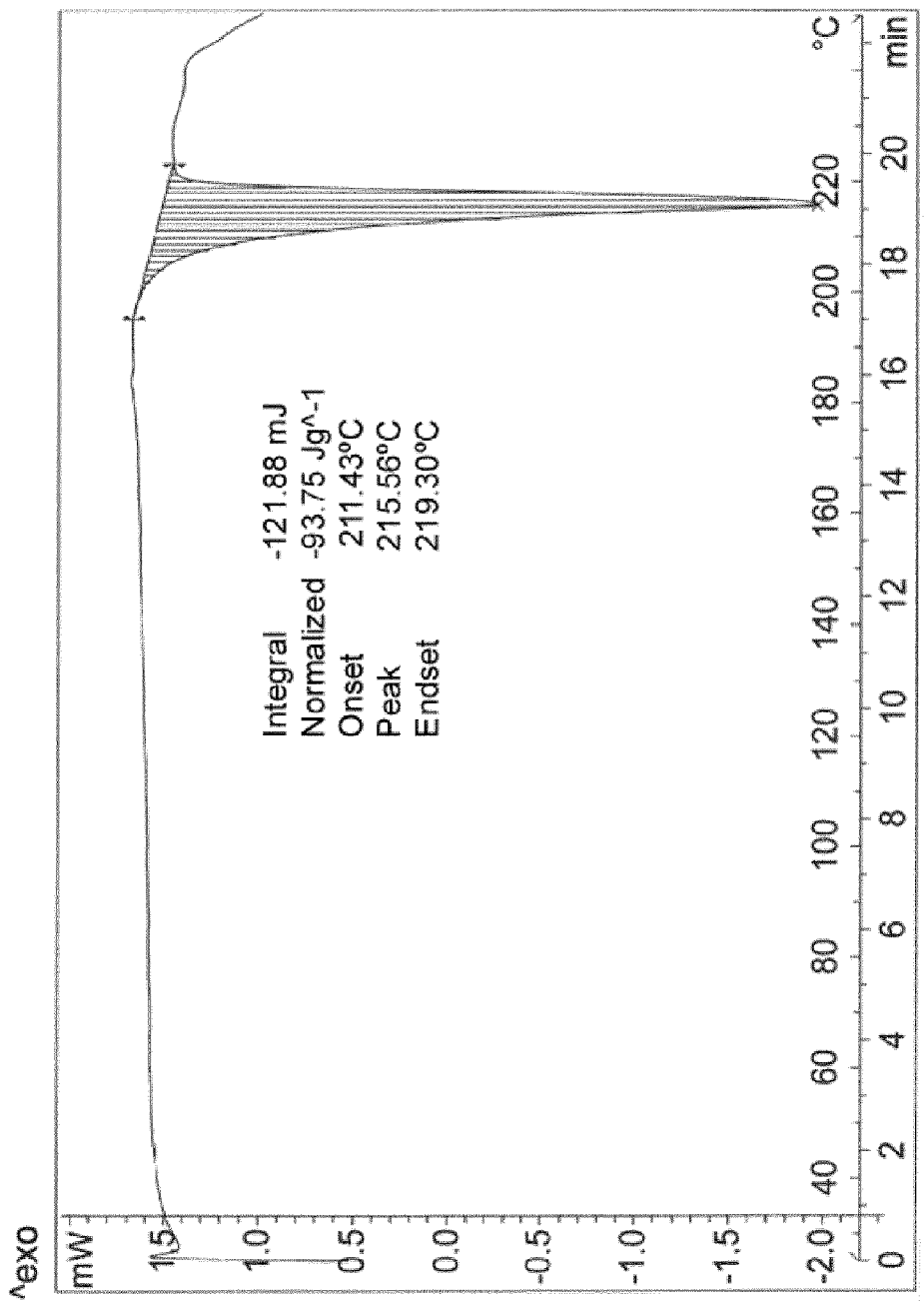
FIG. 10 shows a DSC pattern obtained for the product of Example 3.
Figure 14:
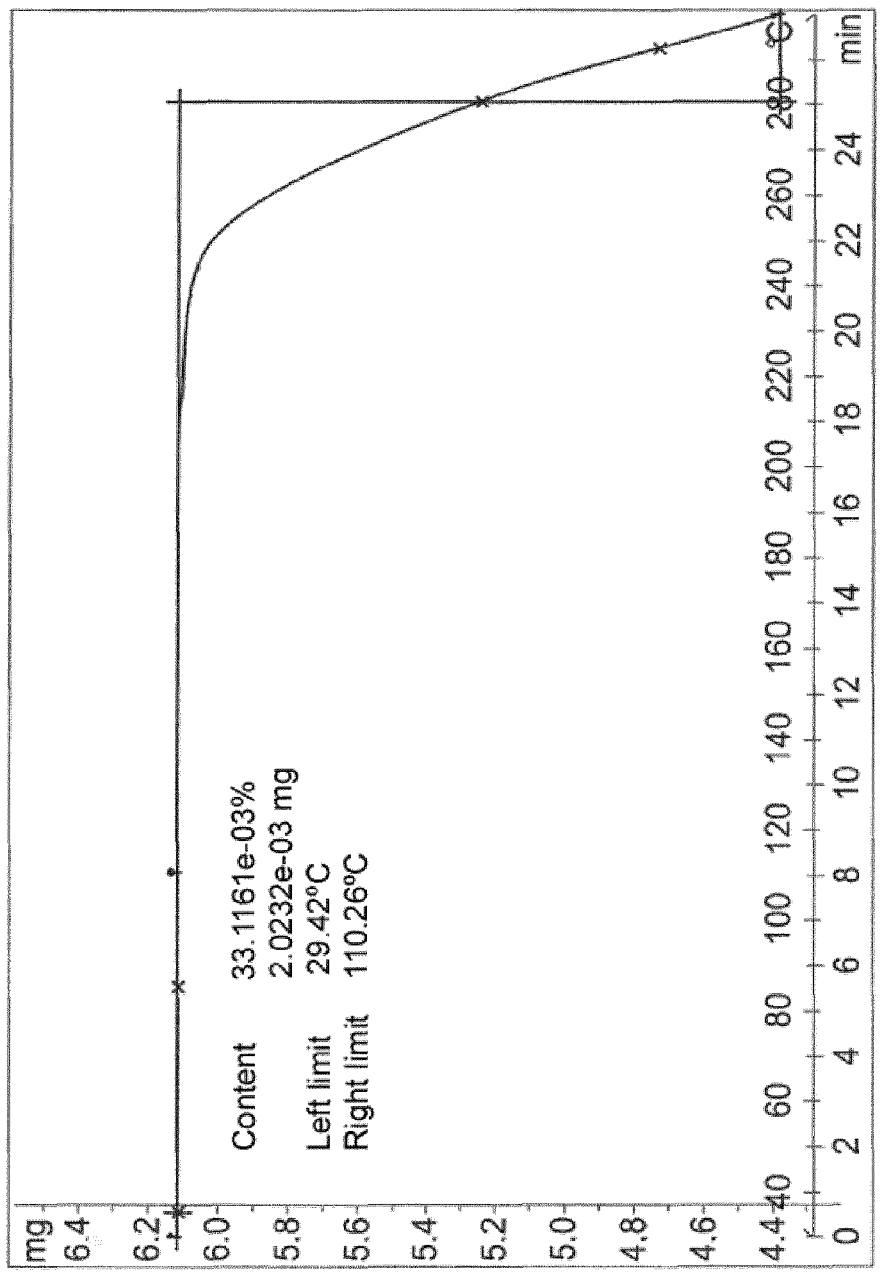
FIG. 14 shows a TGA pattern obtained for the product of Example 3.

5.0 g (9.893 mmoles) of sitagliptin sulfate salt were dissolved at the approximate temperature of 50° C. in a mixture of 100 ml of 2-propanol and 12.5 ml of water. The solution thus obtained was slowly cooled to the approximate temperature of 25° C. the appearance of a white precipitate being observed. It was maintained for 3 hours at said temperature. The solid obtained was filtered and washed in the filter with 2-propanol (2×5 ml). The wet product was dried in a vacuum oven at 40° C. to yield 3.0 g (5.936 mmoles) of a white crystalline solid (60.0%). The DSC of the product (FIG. 10) shows an endothermic signal at 215.6° C.; The product thus obtained has an XRPD pattern depicted in FIG. 4 corresponding to form M of sitagliptin sulfate. The water content determined by TGA (FIG. 14) is 0.03%.

Example 4

Figure 5:
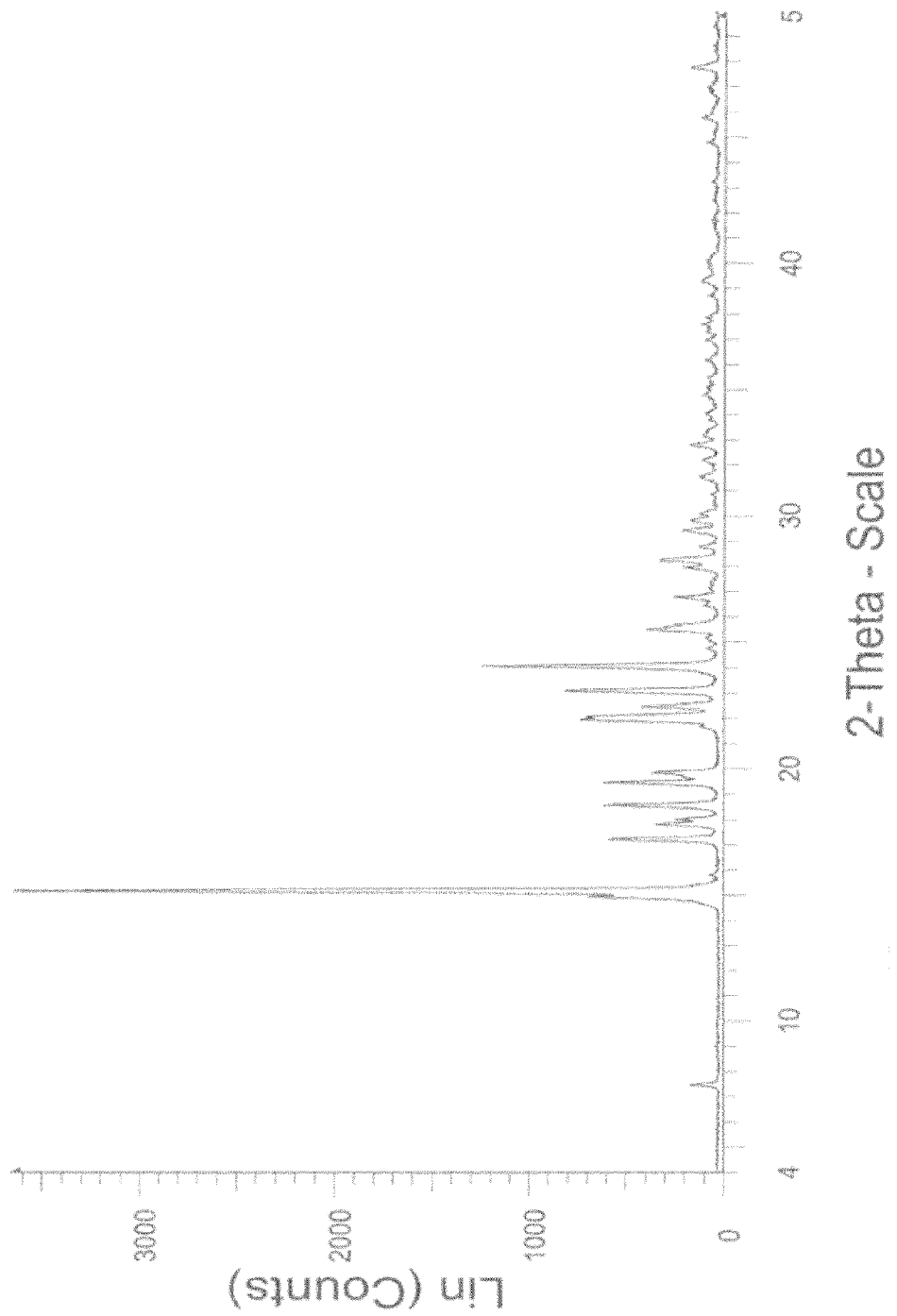
FIG. 5 shows an XRPD pattern obtained for the product of Example 4.
Figure 15:
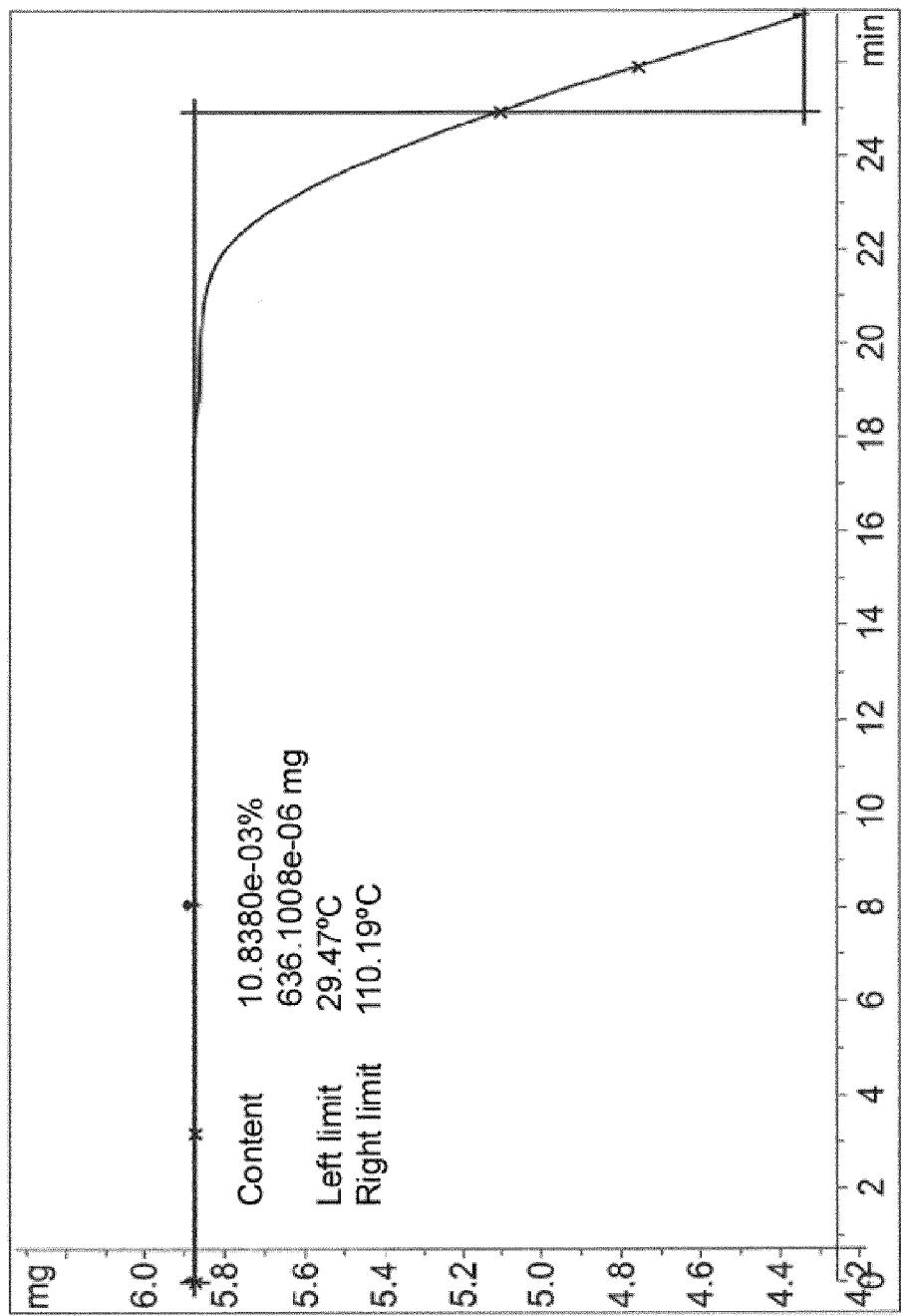
FIG. 15 shows a TGA pattern obtained for the product of Example 4.

2.5 g (4.947 mmoles) of sitagliptin sulfate salt were dissolved at the approximate temperature of 50° C. in a mixture of 37.5 ml of absolute ethanol and 3 ml of water. The solution thus obtained was slowly cooled to the approximate temperature of 25° C., the appearance of a white precipitate being observed. It was maintained for 3 hours at said temperature. The solid obtained was filtered and washed in the filter with absolute ethanol (2×2.5 ml). The wet product was dried in a vacuum oven at 40° C. to yield 1.6 g (3.166 mmoles) of a white crystalline solid (64.0%). The DSC of the product obtained showed an endothermic signal at 216.0° C. The product thus obtained has an XRPD pattern corresponding to form M of sitagliptin sulfate (FIG. 5). The water content determined by TGA (FIG. 15) is 0.01%.

Example 5

Figure 6:
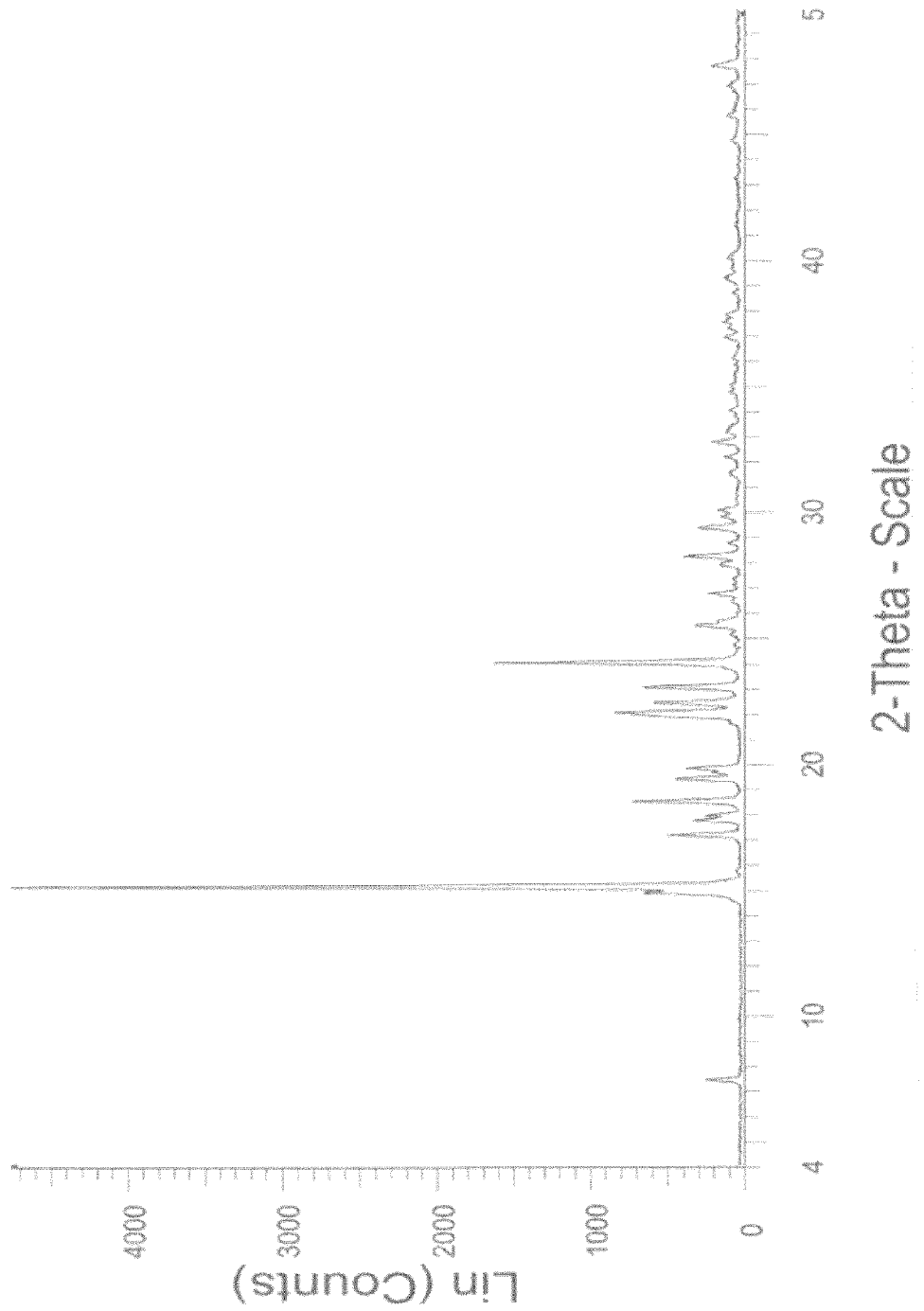
FIG. 6 shows an XRPD pattern obtained for the product of Example 5.
Figure 11:
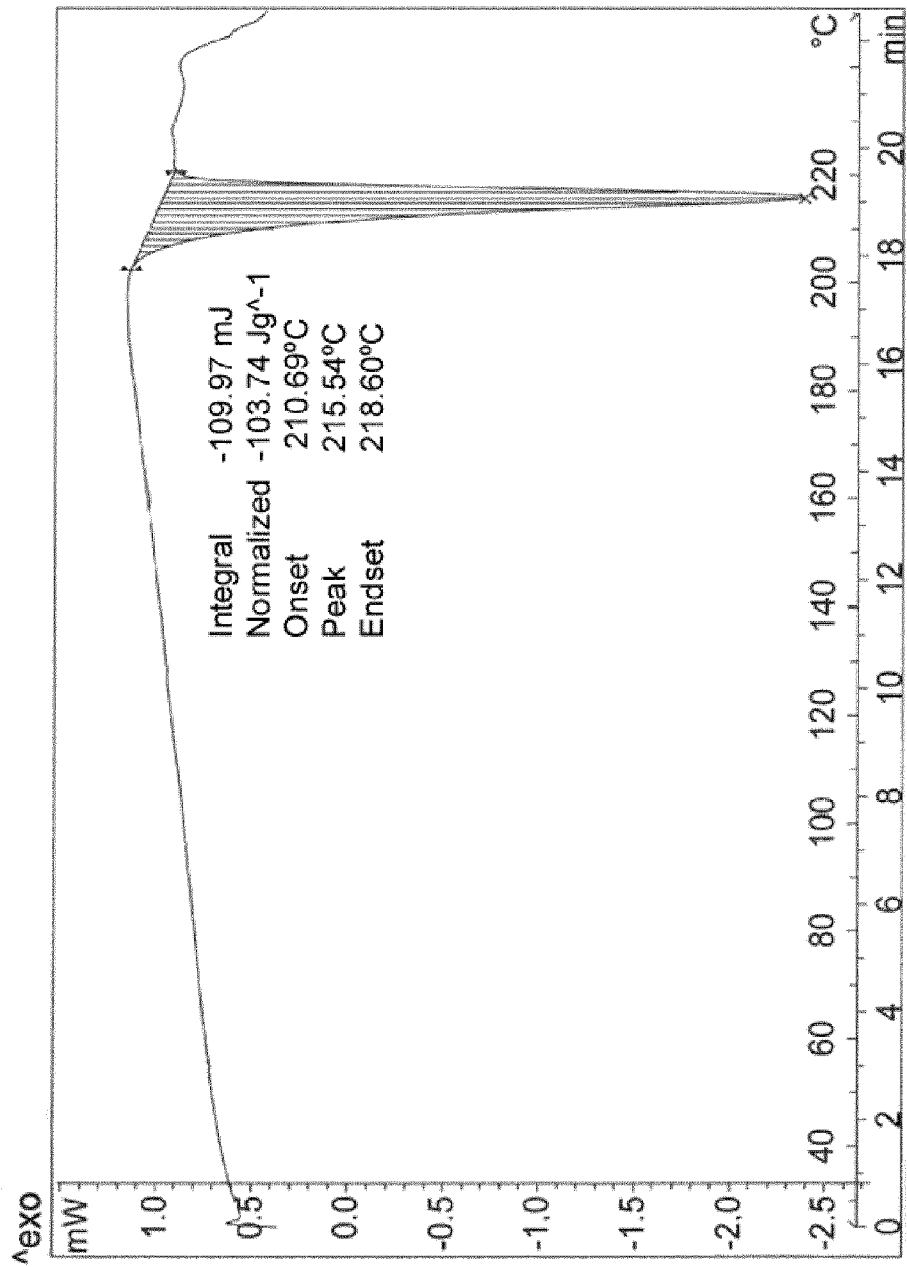
FIG. 11 shows a DSC pattern obtained for the product of Example 5.
Figure 16:
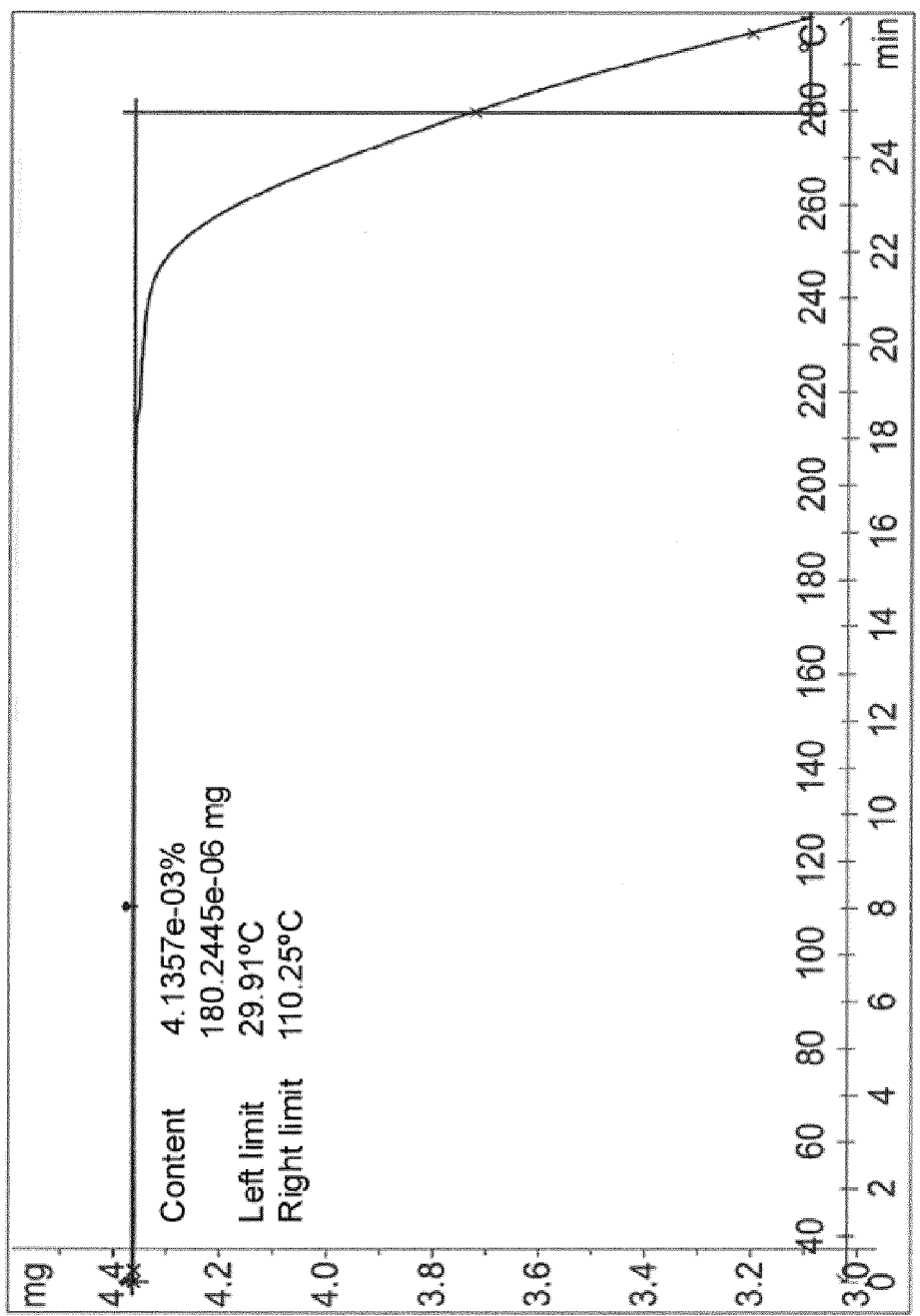
FIG. 16 shows a TGA pattern obtained for the product of Example 5.

37.5 g (74.20 mmoles) of sitagliptin sulfate salt were dissolved at the approximate temperature of 50° C. in a mixture of 560 ml of absolute ethanol and 86 ml of water. The solution thus obtained was slowly cooled to the approximate temperature of 25° C., the appearance of a white precipitate being observed. It was maintained for 4 hours at said temperature. The solid obtained was filtered and washed in the filter with absolute ethanol (3×25 ml). The wet product was dried in a vacuum oven at 40° C. to yield 24.3 g (48.08 mmoles) of a white crystalline solid (64.8%). Purity (by means of HPLC): 99.8%. The product thus obtained has an XRPD pattern depicted in FIG. 6 corresponding to form M of sitagliptin sulfate. The DSC of the product (FIG. 11) shows an endothermic signal at 215.5° C. The water content determined by TGA (FIG. 16) is 0.004%.

Example 6

A stability study of the M form of sitagliptin sulfate was performed under conditions of the European Pharmacopeia Ed. 6.0 Section 5.11, i.e., the degree of hydration was measured at 80% relative humidity (RH) at a temperature of 25° C. Additionally, the degree of hydration was also measured at 97% relative humidity (RH) at a temperature of 25° C.

The results are shown in Table 1, wherein the higroscopicity (expressed as the water content by means of weight difference, following the procedure described in European Pharmacopeia Ed. 6.0 Section 5.11) of samples of 1 g of sitagliptin sulfate polymorph M of the present invention after storage at 1 day, 3 days, 7 days, 14 days and 21 days at 80% RH and 97% RH, respectively. In view of these results, it can be concluded that the M form of sitagliptin sulfate was non-hygroscopic under the conditions mentioned above according to the criteria of the European Pharmacopeia Ed. 6.0 Section 5.11, i.e., the degree of hydration is less than 0.2%.

TABLE 1

| Time | Higroscopicity RH 80% | Higroscopicity RH 97% |
|---|---|---|
| 1 day | 0.07% | 0.05% |
| 3 days | 0.10% | 0.08% |
| 7 days | 0.12% | 0.06% |
| 14 days | 0.10% | 0.06% |
| 21 days | 0.07% | 0.07% |

Figure 17:
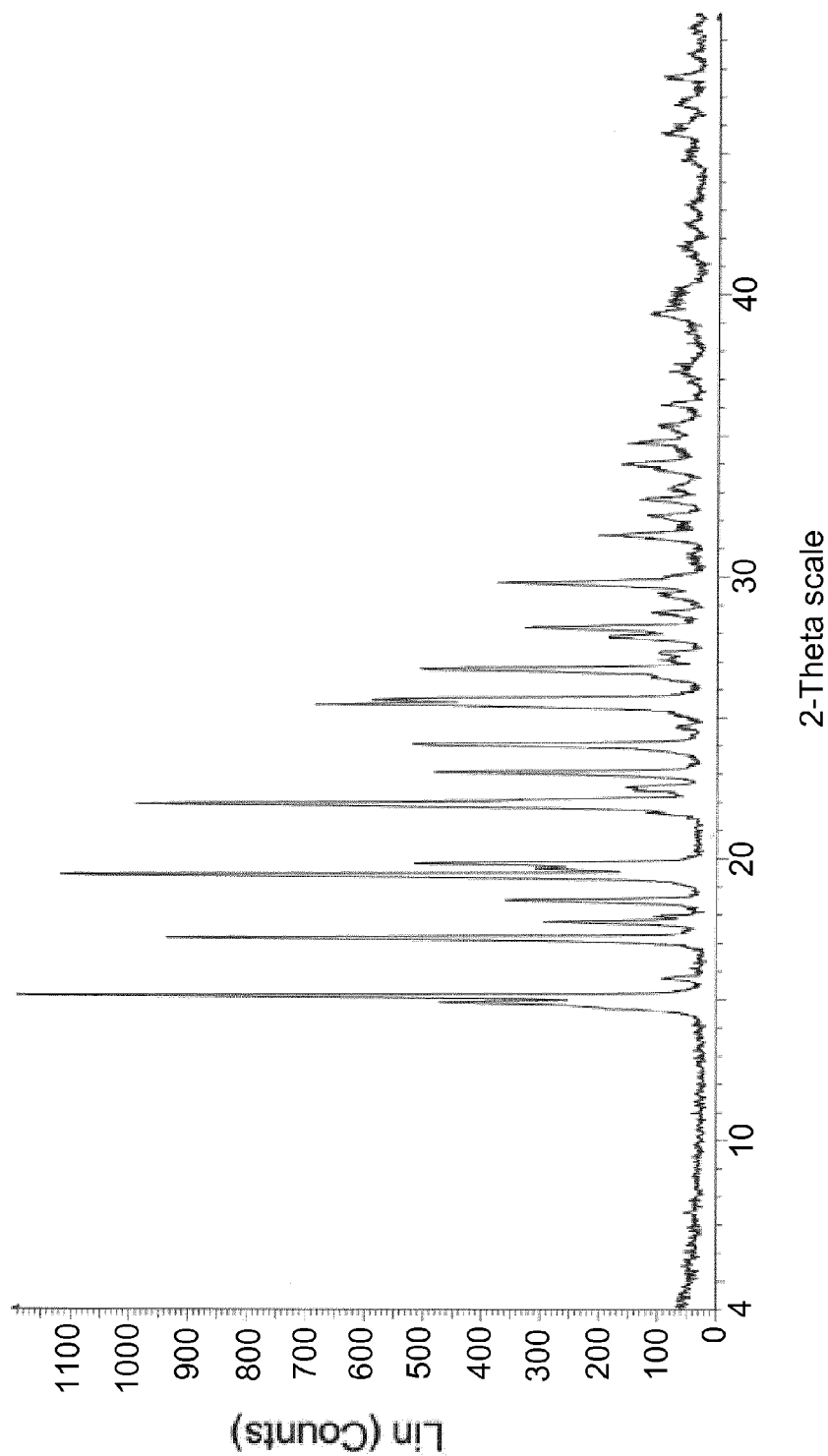
FIG. 17 shows an XRPD pattern obtained for the product of Example 6 after storage at 25° C. and 80% RH during 21 days.
Figure 18:
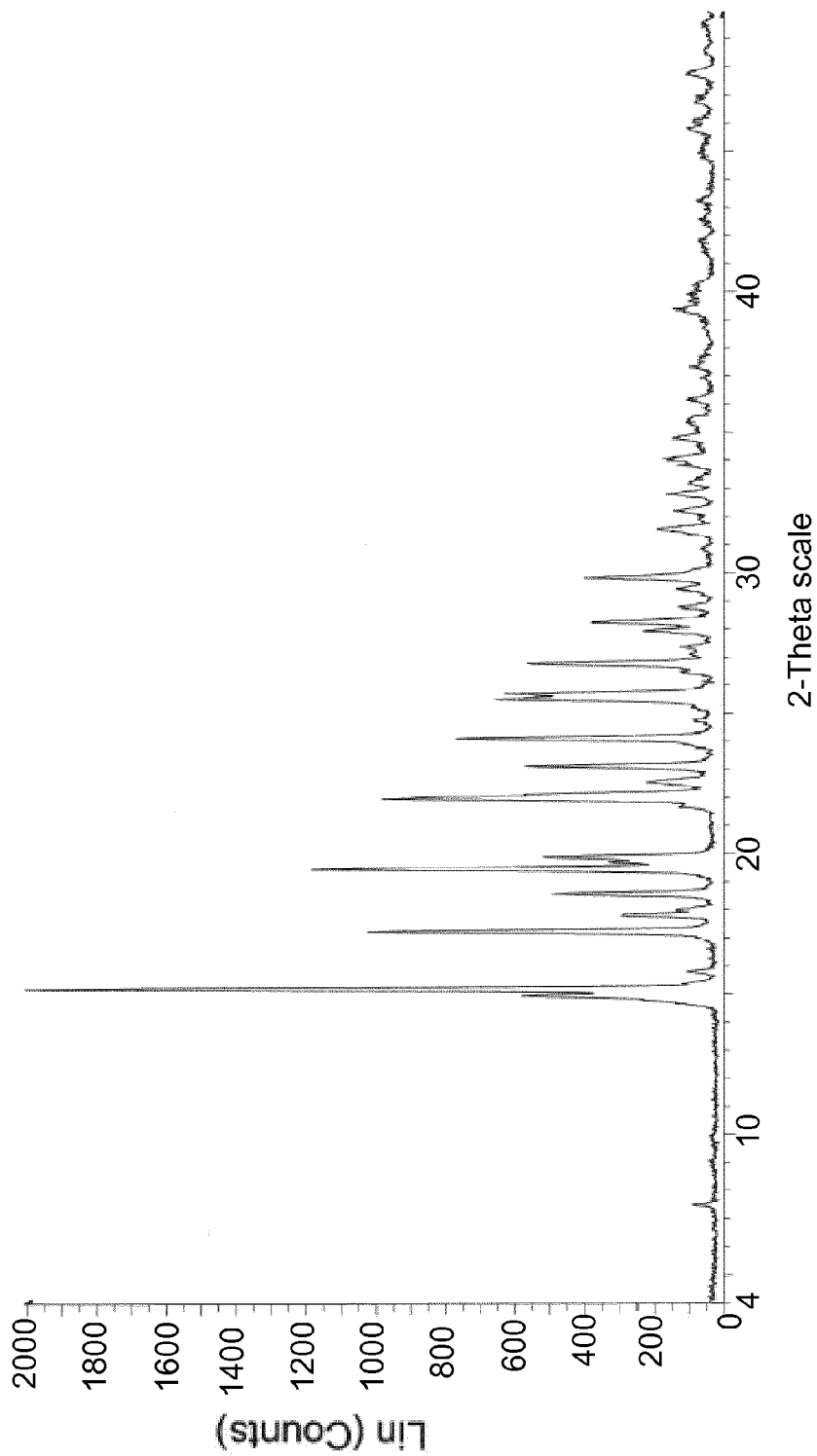
FIG. 18 shows an XRPD pattern obtained for the product of Example 6 after storage at 25° C. and 97% RH during 21 days.

The crystalline form of sitagliptin sulfate after 21 days at a relative humidity of 80% and 97%, respectively, were analyzed by means of X-ray diffraction. The XRPD pattern are provided in FIG. 17 (RH 80%) and FIG. 18 (RH 97%), both corresponding to form M of sitagliptin sulfate.

Example 7

Accelerated stability study of the M form of sitagliptin sulfate was performed under the following conditions: temperature of 40° C.±2° C. and relative humidity (RH) of 75%±5%. The water content of the sample was determined at the beginning of the study, at 3 months and at 6 months, by means of Karl-Fisher. The results are shown in Table 2.

TABLE 2

| Time | Water content |
|---|---|
| Initial | 0.09% |
| 3 months | 0.09% |
| 6 months | 0.01% |

Figure 19:
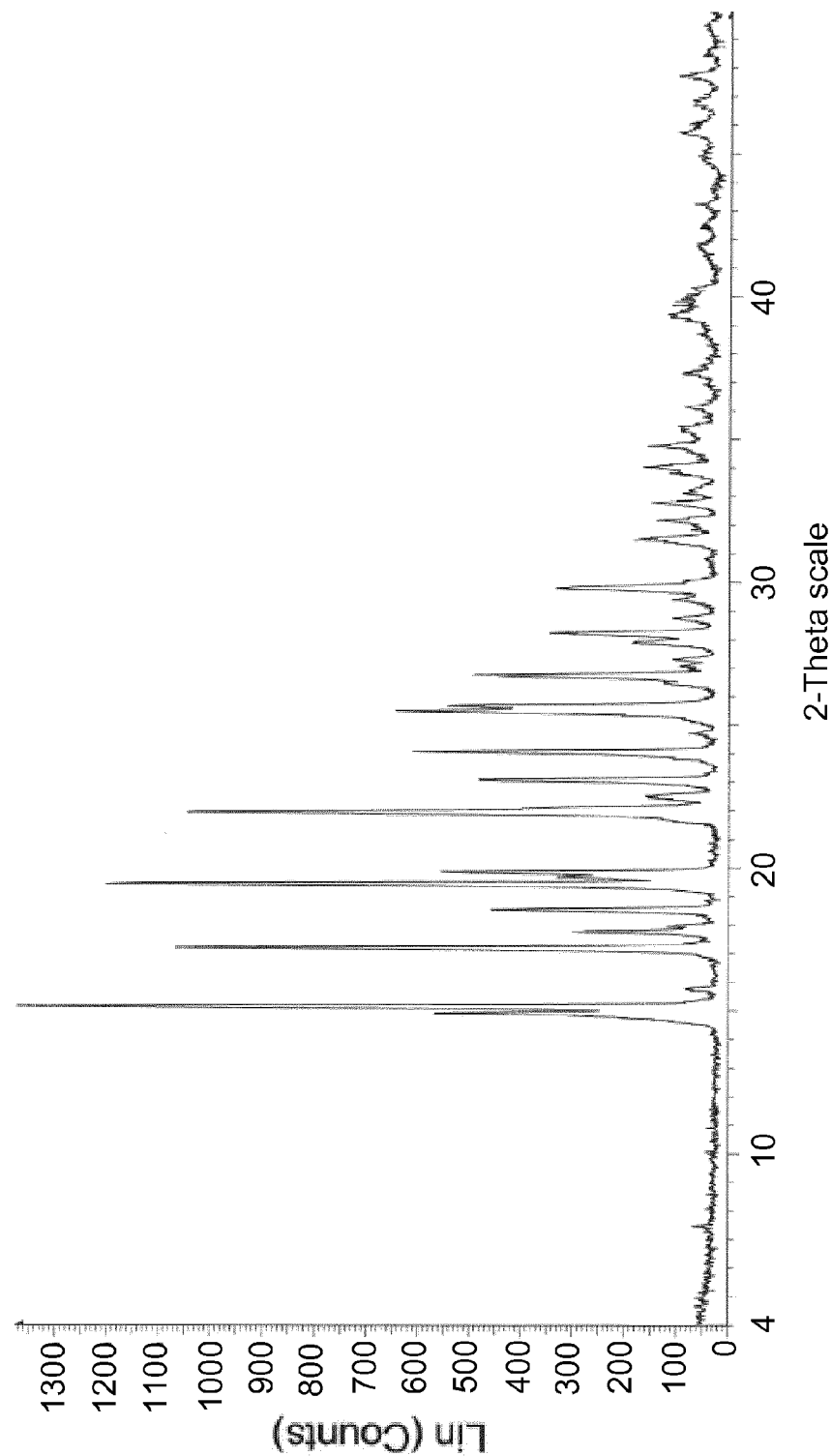
FIG. 19 shows an XRPD pattern obtained for the product of Example 7 at 6 months of accelerated stability conditions.

The crystalline form of sitagliptin sulfate after 6 months was analyzed by means of X-ray diffraction. The XRPD pattern is provided in FIG. 19, corresponding to form M of sitagliptin sulfate.

Examples 8-27

Pharmaceutical compositions comprising sitagliptin sulfate polymorph M were prepared. Tables 3-5 provide the amount (in mg) of the components of tablets prepared by direct compression. Table 6 provides the amount (in mg) of the components of tablets prepared by wet granulation.

Brief description of direct compression:

1. blending/mixing sitagliptin sulfate polymorph M of the present invention with excipients;

2. optionally sieving;

3. compressing direct into tablets without further granulation or other steps;

4. optionally coating.

Brief Description of Wet Granulation:

1. sitagliptin sulfate polymorph M of the present invention or a mixture of sitagliptin sulfate polymorph M of the present invention with excipients is granulated with a liquid such as purified water and pharmaceutically acceptable organic solvents (e.g. ethanol, acetone, isopropanol), preferably purified water;

2. the granules are dried by removing the liquid in e.g. a fluid bed;

3. the granules are lubricated and compressed into tablets;

4. optionally coating.

TABLE 3

Tablets prepared by direct compression. Amounts are given in mg.

| | Example | | | | | | |
|---|---|---|---|---|---|---|---|
| | 8 | 9 | 10 | 11 | 12 | 13 | 14 |
| Tablets comprising sitagliptin sulfate polymorph M | | | | | | | |
| Sitagliptin sulfate polymorph M* | 32.1 | 32.1 | 32.1 | 32.1 | 32.1 | 32.1 | 32.1 |
| Calcium hydrogenphosphate anhydrous | 30.9 | | | | | | |
| Mannitol (direct compression grade (DC)) | | 61.9 | 61.9 | 61.9 | 30.9 | 30.9 | 30.9 |
| Microcrystalline cellulose | 30.9 | | | | 33.9 | 33.9 | 31.9 |
| Croscarmellose sodium | 2.0 | 2.0 | 2.0 | 2.0 | 2.0 | 2.0 | 2.0 |
| Sodium stearyl fumarate | 3.0 | | | | | | 2.0 |
| Magnesium stearate | 1.0 | | | 1.0 | 1.0 | 1.0 | 1.0 |
| Colloidal silicon dioxide | 1.0 | | | 3.0 | | 0.5 | |
| Sodium lauryl sulphate | 1.0 | | 2.0 | | | | |
| Total core | 101.9 | 96.0 | 98.0 | 100.0 | 99.9 | 100.4 | 99.9 |

*Equivalent to 25 mg/tablet of sitagliptin free base

TABLE 4

Tablets prepared by direct compression. Amounts are given in mg.

| Example | 15 | 16 | 17 | 18 | 19 |
|---|---|---|---|---|---|
| Tablets comprising sitagliptin sulfate polymorph M | | | | | |
| Sitagliptin sulfate polymorph M* | 32.1 | 32.1 | 32.1 | 32.1 | 32.1 |
| Lactose (DC) | | | 30.9 | 30.6 | 30.6 |
| Mannitol (DC) | 30.9 | 30.9 | | | |
| Polyvinyl pirrolidone (Povidone K 25) | | | | | 0.5 |
| Microcrystalline cellulose | 30.9 | 31.9 | 32.4 | 32.4 | 32.4 |
| Croscarmellose sodium | 2.0 | 2.0 | 2.0 | 2.0 | 2.0 |
| Sodium stearyl fumarate | 3.0 | 2.0 | 1.0 | 3.0 | 3.0 |
| Magnesium stearate | 1.0 | 1.0 | 1.0 | 1.0 | 1.0 |
| Colloidal silicon dioxide | | | 0.5 | | |
| Total core | 99.9 | 99.9 | 99.9 | 101.1 | 101.6 |

*Equivalent to 25 mg/tablet of sitagliptin free base

TABLE 5

Tablets prepared by direct compression. Amounts are given in mg.

| Example | 20 | 21 | 22 |
|---|---|---|---|
| Film coated tablets comprising sitagliptin sulfate polymorph M | | | |
| Sitagliptin sulfate polymorph M | 31.0[a] | 31.0[a] | 124.0[b] |
| Prosolv Easytab (mixture of microcrystalline cellulose, sodium starch glycolate, silicon dioxide and sodium stearyl fumarate) | | | |
| Mannitol (DC) | | | 122.4 |
| Sorbitol (DC) | | 30.6 normal | |
| Microcrystalline cellulose | 63.0 | 32.4 | 129.6 |
| Croscarmellose sodium | 2.0 | 2.0 | 8.0 |
| Sodium stearyl fumarate | 3.0 | 3.0 | 12.0 |
| Magnesium stearate | 1.0 | 1.0 | 4.0 |
| Total core | 100.0 | 100.0 | 400.0 |
| Coating: Opadry II 85F23813 (mixture of polyvinyl alcohol, polyethylene glycol, iron oxide, titanium oxide and talc) | 4.0 | 4.0 | 16.0 |

[a]Equivalent to 25 mg/tablet of sitagliptin free base
[b]Equivalent to 100 mg/tablet of sitagliptin free base

TABLE 6

Tablets prepared by wet granulation in high shear and in fluid bed dryer (FBD). Amounts are given in mg.

| Example | 23 | 24 | 25 | 26 | 27 |
|---|---|---|---|---|---|
| Film coated tablets comprising sitagliptin sulfate polymorph M | | | | | |
| | Granulated in high shear | Granulated in FBD | Granulated in FBD | Granulated in FBD | Granulated in FBD |
| Sitagliptin sulfate polymorph M* | 124.0 | 124.0 | 124.0 | 124.0 | 124.0 |
| Lactose | 102.4 | 102.4 | | | |
| Isomalt | | | 102.4 | | |
| Sorbitol | | | | 102.4 | |
| Mannitol | | | | | 102.4 |
| Polyvinylpirrolidone (Povidone K 25) | 20.0 | 20.0 | 20.0 | 20.0 | 20.0 |
| Microcrystalline cellulose | 129.6 | 129.6 | 129.6 | 129.6 | 129.6 |
| Crosscarmellose sodium | 8.0 | 8.0 | 8.0 | 8.0 | 8.0 |
| Sodium stearyl fumarate | 12.0 | 12.0 | 12.0 | 12.0 | 12.0 |
| Magnesium stearate | 4.0 | 4.0 | 4.0 | 4.0 | 4.0 |
| Total core | 400.0 | 400.0 | 400.0 | 400.0 | 400.0 |
| Coating: Opadry II 85F23813 (mixture of polyvinyl alcohol, polyethylene glycol, iron oxide, titanium oxide and talc) | 16.0 | 16.0 | 16.0 | 16.0 | 16.0 |

*Equivalent to 100 mg/tablet of sitagliptin free base

What is claimed is:

1. A crystalline form of sitagliptin sulfate (1:1) characterized by an X-ray powder diffraction pattern having peaks at 2θ values equal to 14.8±0.2°, 15.1±0.2°, 17.1±0.2°, 19.4±0.2°, 21.9±0.2°, 24.0±0.2° and 25.4±0.2°.

2. The crystalline form according to claim 1, characterized in that it has an X-ray diffraction pattern further comprising peaks at the following 2θ values equal to 18.5±0.2°, 19.8±0.2°, 23.0±0.2° and 26.7±0.2°.

3. The crystalline form according to claim 1, wherein the crystalline form comprises a percentage of water less than 0.05% determined by thermal gravimetric analysis.

4. The crystalline form according to claim 1, wherein the crystalline form comprises a differential scanning calorimetry (DSC) thermogram with an endothermic peak at 216.0±1.0° C.

5. A method for preparing the crystalline form of sitagliptin sulfate of claim 1 comprising the following steps:
   a) providing sitagliptin base,
   b) preparing a sitagliptin base suspension or solution in a mixture comprising water and one or more water-miscible organic solvents,
   c) adding a sulfuric acid ($H_2SO_4$) solution in one or more of the water-miscible organic solvents to the suspension or to the solution obtained in step b) such that the molar ratio of $H_2SO_4$ to sitagliptin base is comprised between 0.9:1 and 1.1:1, and
   d) optionally, adding crystals from the crystalline form of sitagliptin sulfate of claim 1 to the suspension,
   such that the ratio of volume (in ml) of organic solvent added in steps b) and c) to weight (in g) of sitagliptin base is between 10:1 and 30:1 and the ratio of volume (in ml) of water added in steps b) and c) to weight (in g) of sitagliptin base is between 1:1 and 5:1.

6. A method for preparing the crystalline form of sitagliptin sulfate of claim 1 comprising the following steps:
   a) providing sitagliptin sulfate,
   b) preparing a sitagliptin sulfate solution in a mixture comprising water and a water-miscible solvent such that the ratio of volume (in ml) of organic solvent to weight (in g) of sitagliptin sulfate is between 10:1 and 30:1 and the ratio of volume (in ml) of water to weight (in g) of sitagliptin sulfate is between 1:1 and 5:1, and
   c) optionally, adding crystals from the crystalline form of sitagliptin sulfate of claim 1 to the suspension.

7. A pharmaceutical composition comprising the crystalline form of sitagliptin sulfate of claim 1 and at least one pharmaceutically acceptable excipient.

8. The pharmaceutical composition according to claim 7 which comprises:
   from 1% to 80% by weight, with respect to the total weight of the composition, of the crystalline form of sitagliptin sulfate;
   from 0% to 99% by weight, with respect to the total weight of the composition, of one or more diluents/fillers;
   from 0% to 20% by weight, with respect to the total weight of the composition, of one or more disintegrants;
   from 0% to 20% by weight, with respect to the total weight of the composition, of one or more glidants and/or lubricants; and
   optionally a film coat;
   with the proviso that at least one pharmaceutically acceptable excipient selected from the group consisting of diluents/fillers, disintegrants, glidants and lubricants, is present in the composition.

9. The pharmaceutical composition according to claim 8, which comprises:
   from 10% to 50% by weight, with respect to the total weight of the composition, of the crystalline form of sitagliptin sulfate;
   from 40% to 80% by weight, with respect to the total weight of the composition, of one or more diluents/fillers;
   from 0% to 10% by weight, with respect to the total weight of the composition, of one or more disintegrants;
   from 0% to 10% by weight, with respect to the total weight of the composition, of one or more glidants and/or lubricants; and
   optionally a film coat.

10. The pharmaceutical composition according to claim 9, which comprises:
    from 20% to 40% by weight, with respect to the total weight of the composition, of the crystalline form of sitagliptin sulfate;
    from 50% to 70% by weight, with respect to the total weight of the composition, of one or more diluents/fillers;
    from 1% to 6% by weight, with respect to the total weight of the composition, of one or more disintegrants;
    from 1% to 6% by weight, with respect to the total weight of the composition, of one or more glidants and/or lubricants; and
    optionally a film coat.

11. The pharmaceutical composition according to claim 7, characterized by being a solid at a temperature of 25° C.

12. The pharmaceutical composition according to claim 7 further comprising metformin.

13. The pharmaceutical composition according to claim 7, further comprising a sulfonylurea selected from the group consisting of tolbutamide, acetohexamide, tolazamide, chlorpropamide, glipizide, glyburide, glimepiride and gliclazide.

14. The pharmaceutical composition according to claim 7, further comprising a peroxisome proliferator-activated receptor gamma (PPARγ) agonist selected from the group consisting of rosiglitazone, pioglitazone and troglitazone.

15. The pharmaceutical composition according to claim 7, further comprising a 3-hydroxy-3-methyl-glutaryl-coenzyme A reductase (HMG-CoA reductase) inhibitor selected from the group consisting of lovastatin, simvastatin, pravastatin, fluvastatin, atorvastatin, rivastatin, itavastatin and rosuvastatin.

16. A method for improving blood glucose control in type 2 diabetes mellitus patients comprising administering the crystalline form of sitagliptin sulfate of claim 1.

17. A method for improving blood glucose control in type 2 diabetes mellitus patients comprising administering the crystalline form of sitagliptin sulfate of claim 1 in combination with metformin.

18. A method for improving the of blood glucose control in type 2 diabetes mellitus patients comprising administering the crystalline form of sitagliptin sulfate of claim 1 in combination with a sulfonylurea selected from the group consisting of tolbutamide, acetohexamide, tolazamide, chlorpropamide, glipizide, glyburide, glimepiride and gliclazide.

19. A method for improving the of blood glucose control in type 2 diabetes mellitus patients comprising administering the crystalline form of sitagliptin sulfate of claim 1 in combination with a peroxisome proliferator-activated receptor gamma (PPARγ) agonist selected from the group consisting of rosiglitazone, pioglitazone and troglitazone.

20. A method for improving the of blood glucose control in type 2 diabetes mellitus patients comprising administering the crystalline form of sitagliptin sulfate of claim 1 in combination with a 3-hydroxy-3-methyl-glutaryl-coenzyme A reductase (HMG-CoA reductase) inhibitor selected from the group consisting of lovastatin, simvastatin, pravastatin, fluvastatin, atorvastatin, rivastatin, itavastatin and rosuvastatin.

* * * * *